United States Patent
Lee et al.

(10) Patent No.: US 9,427,574 B2
(45) Date of Patent: Aug. 30, 2016

(54) IMPLANTABLE LEAD AFFIXATION STRUCTURE FOR NERVE STIMULATION TO ALLEVIATE BLADDER DYSFUNCTION AND OTHER INDICATION

(71) Applicant: Axonics Modulation Technologies, Inc., Irvine, CA (US)

(72) Inventors: Henry Lee, Arcadia, CA (US); Alexander Hwu, Anaheim, CA (US)

(73) Assignee: AXONICS MODULATION TECHNOLOGIES, INC., Irvine, CA (US)

(*) Notice: Subject to any disclaimer, the term of this patent is extended or adjusted under 35 U.S.C. 154(b) by 0 days.

(21) Appl. No.: 14/991,649

(22) Filed: Jan. 8, 2016

(65) Prior Publication Data

US 2016/0121105 A1    May 5, 2016

Related U.S. Application Data

(63) Continuation of application No. 14/827,074, filed on Aug. 14, 2015.

(60) Provisional application No. 62/038,122, filed on Aug. 15, 2014, provisional application No. 62/110,274, filed on Jan. 30, 2015.

(51) Int. Cl.
*A61N 1/05* (2006.01)
*A61N 1/36* (2006.01)
(Continued)

(52) U.S. Cl.
CPC ........... *A61N 1/0558* (2013.01); *A61N 1/3606* (2013.01); *A61N 1/36007* (2013.01);
(Continued)

(58) Field of Classification Search
CPC ........... A61N 1/0558; A61N 1/36007; A61N 1/3606; B23K 2203/14; B23K 2203/18; B23K 26/242; B23K 26/38; B23K 26/40; B29C 45/14065; B29C 45/14598; B29C 45/14778; B29L 2031/753
See application file for complete search history.

(56) References Cited

U.S. PATENT DOCUMENTS 3,646,940 A    3/1972    Timm et al.
4,019,518 A    4/1977    Maurer et al.
(Continued)

FOREIGN PATENT DOCUMENTS

EP    1680182 A1    7/2006
EP    1680182 B1    7/2006
(Continued)

OTHER PUBLICATIONS

Bosch, J., et al., Sacral (S3) Segmental Nerve Stimulation as a Treatment for Urge Incontinence in Patients With Detrusor Instability: Results of Chronic Electrical Stimulation Using an Implantable Neural Prosthesis, The Journal of Urology, Aug. 1995, vol. 154, pp. 504-507.
(Continued)

*Primary Examiner* — Catherine Voorhees
(74) *Attorney, Agent, or Firm* — Kilpatrick Townsend & Stockton LLP; Kenneth R. Shurtz, Esq.

(57) ABSTRACT

Anchoring devices and methods for affixing an implanted lead of a neurostimulation system at a target location in a patient are provided herein. Such anchoring devices includes a helical body having a plurality of tines extending laterally outward from the lead when deployed that engage tissue to inhibit axial movement of the implanted lead. The plurality of tines are biased towards the laterally extended deployed configuration and fold inward towards the lead to a delivery configuration to facilitate delivery of the lead through a sheath. The tines may be angled in a proximal direction or in both proximal and distal directions and may include various features to assist in visualization and delivery of the lead. The anchor may be formed according to various methods, including laser cutting of a tubular section along with heat or reflow to set the material with the anchor in the deployed configuration and injection molding.

25 Claims, 21 Drawing Sheets

(51) Int. Cl.
  *B23K 26/38* (2014.01)
  *B23K 26/40* (2014.01)
  *B29C 45/14* (2006.01)
  *B29L 31/00* (2006.01)

(52) U.S. Cl.
  CPC ............. *B23K26/242* (2015.10); *B23K 26/38* (2013.01); *B23K 26/40* (2013.01); *B29C 45/14065* (2013.01); *B29C 45/14598* (2013.01); *B23K 2203/14* (2013.01); *B23K 2203/18* (2013.01); *B23K 2203/26* (2015.10); *B29C 45/14778* (2013.01); *B29L 2031/753* (2013.01)

(56) References Cited

U.S. PATENT DOCUMENTS

| | | | |
|---|---|---|---|
| 4,044,774 | A | 8/1977 | Corbin et al. |
| 4,340,062 | A | 7/1982 | Thompson et al. |
| 4,558,702 | A | 12/1985 | Barreras et al. |
| 4,744,371 | A | 5/1988 | Harris |
| 5,366,493 | A | 11/1994 | Scheiner et al. |
| 5,690,693 | A | 11/1997 | Wang et al. |
| 5,702,428 | A | 12/1997 | Tippey et al. |
| 5,702,431 | A | 12/1997 | Wang et al. |
| 5,735,887 | A | 4/1998 | Barreras, Sr. et al. |
| 5,741,316 | A | 4/1998 | Chen et al. |
| 5,876,423 | A | 3/1999 | Braun |
| 6,027,456 | A | 2/2000 | Feler et al. |
| 6,035,237 | A | 3/2000 | Schulman et al. |
| 6,052,624 | A | 4/2000 | Mann |
| 6,055,456 | A | 4/2000 | Gerber |
| 6,057,513 | A | 5/2000 | Ushikoshi et al. |
| 6,067,474 | A | 5/2000 | Schulman et al. |
| 6,076,017 | A | 6/2000 | Taylor et al. |
| 6,172,556 | B1 | 1/2001 | Prentice |
| 6,178,353 | B1 | 1/2001 | Griffith et al. |
| 6,191,365 | B1 | 2/2001 | Avellanet |
| 6,208,894 | B1 | 3/2001 | Schulman et al. |
| 6,212,431 | B1 | 4/2001 | Hahn et al. |
| 6,221,513 | B1 | 4/2001 | Lasater |
| 6,246,911 | B1 | 6/2001 | Seligman |
| 6,249,703 | B1 | 6/2001 | Stanton et al. |
| 6,265,789 | B1 | 7/2001 | Honda et al. |
| 6,306,100 | B1 | 10/2001 | Prass |
| 6,315,721 | B2 | 11/2001 | Schulman et al. |
| 6,354,991 | B1 | 3/2002 | Gross et al. |
| 6,360,750 | B1 | 3/2002 | Gerber et al. |
| 6,393,325 | B1 | 5/2002 | Mann et al. |
| 6,438,423 | B1 | 8/2002 | Rezai et al. |
| 6,442,434 | B1 | 8/2002 | Zarinetchi et al. |
| 6,466,817 | B1 | 10/2002 | Kaula et al. |
| 6,505,075 | B1 | 1/2003 | Weiner |
| 6,516,227 | B1 | 2/2003 | Meadows et al. |
| 6,584,355 | B2 | 6/2003 | Stessman |
| 6,600,954 | B2 | 7/2003 | Cohen et al. |
| 6,609,031 | B1 | 8/2003 | Law et al. |
| 6,609,032 | B1 | 8/2003 | Woods et al. |
| 6,652,449 | B1 | 11/2003 | Gross et al. |
| 6,662,051 | B1 | 12/2003 | Eraker et al. |
| 6,721,603 | B2 | 4/2004 | Zabara et al. |
| 6,735,474 | B1 | 5/2004 | Loeb et al. |
| 6,745,077 | B1 | 6/2004 | Griffith et al. |
| 6,792,314 | B2 * | 9/2004 | Byers ................ A61N 1/0543 607/116 |
| 6,809,701 | B2 | 10/2004 | Amundson et al. |
| 6,836,684 | B1 | 12/2004 | Rijkhoff et al. |
| 6,847,849 | B2 * | 1/2005 | Mamo ................ A61N 1/0551 607/117 |
| 6,892,098 | B2 | 5/2005 | Ayal et al. |
| 6,895,280 | B2 | 5/2005 | Meadows et al. |
| 6,896,651 | B2 | 5/2005 | Gross et al. |
| 6,901,287 | B2 | 5/2005 | Davis et al. |
| 6,941,171 | B2 | 9/2005 | Mann et al. |
| 6,971,393 | B1 | 12/2005 | Mamo et al. |
| 6,989,200 | B2 | 1/2006 | Byers et al. |
| 6,990,376 | B2 | 1/2006 | Tanagho et al. |
| 6,999,819 | B2 | 2/2006 | Swoyer et al. |
| 7,051,419 | B2 | 5/2006 | Schrom et al. |
| 7,054,689 | B1 | 5/2006 | Whitehurst et al. |
| 7,069,081 | B2 | 6/2006 | Biggs et al. |
| 7,127,298 | B1 | 10/2006 | He et al. |
| 7,142,925 | B1 | 11/2006 | Bhadra et al. |
| 7,146,219 | B2 | 12/2006 | Sieracki et al. |
| 7,151,914 | B2 | 12/2006 | Brewer |
| 7,167,749 | B2 | 1/2007 | Biggs et al. |
| 7,177,690 | B2 | 2/2007 | Woods et al. |
| 7,177,698 | B2 | 2/2007 | Klosterman et al. |
| 7,181,286 | B2 | 2/2007 | Sieracki et al. |
| 7,187,978 | B2 | 3/2007 | Malek et al. |
| 7,191,005 | B2 | 3/2007 | Stessman |
| 7,212,110 | B1 | 5/2007 | Martin et al. |
| 7,225,032 | B2 | 5/2007 | Schmeling et al. |
| 7,231,254 | B2 | 6/2007 | DiLorenzo |
| 7,234,853 | B2 | 6/2007 | Givoletti |
| 7,245,972 | B2 | 7/2007 | Davis |
| 7,286,880 | B2 | 10/2007 | Olson et al. |
| 7,305,268 | B2 | 12/2007 | Gliner et al. |
| 7,317,948 | B1 | 1/2008 | King et al. |
| 7,324,852 | B2 | 1/2008 | Barolat et al. |
| 7,324,853 | B2 | 1/2008 | Ayal et al. |
| 7,328,068 | B2 | 2/2008 | Spinelli et al. |
| 7,330,764 | B2 | 2/2008 | Swoyer et al. |
| 7,359,751 | B1 | 4/2008 | Erickson et al. |
| 7,369,894 | B2 | 5/2008 | Gerber |
| 7,386,348 | B2 | 6/2008 | North et al. |
| 7,387,603 | B2 | 6/2008 | Gross et al. |
| 7,396,265 | B2 | 7/2008 | Darley et al. |
| 7,415,308 | B2 | 8/2008 | Gerber et al. |
| 7,444,181 | B2 | 10/2008 | Shi et al. |
| 7,450,991 | B2 | 11/2008 | Smith et al. |
| 7,460,911 | B2 | 12/2008 | Cosendai et al. |
| 7,463,928 | B2 | 12/2008 | Lee et al. |
| 7,470,236 | B1 | 12/2008 | Kelleher et al. |
| 7,483,752 | B2 | 1/2009 | Von Arx et al. |
| 7,496,404 | B2 | 2/2009 | Meadows et al. |
| 7,515,967 | B2 | 4/2009 | Phillips et al. |
| 7,532,936 | B2 | 5/2009 | Erickson et al. |
| 7,539,538 | B2 | 5/2009 | Parramon et al. |
| 7,551,960 | B2 | 6/2009 | Forsberg et al. |
| 7,555,346 | B1 | 6/2009 | Woods et al. |
| 7,565,203 | B2 | 7/2009 | Greenberg et al. |
| 7,578,819 | B2 | 8/2009 | Bleich et al. |
| 7,580,752 | B2 | 8/2009 | Gerber et al. |
| 7,582,053 | B2 | 9/2009 | Gross et al. |
| 7,617,002 | B2 | 11/2009 | Goetz |
| 7,640,059 | B2 | 12/2009 | Forsberg et al. |
| 7,643,880 | B2 | 1/2010 | Tanagho et al. |
| 7,676,275 | B1 | 3/2010 | Farazi et al. |
| 7,706,889 | B2 | 4/2010 | Gerber et al. |
| 7,720,547 | B2 | 5/2010 | Denker et al. |
| 7,725,191 | B2 | 5/2010 | Greenberg et al. |
| 7,734,355 | B2 | 6/2010 | Cohen et al. |
| 7,738,963 | B2 | 6/2010 | Hickman et al. |
| 7,738,965 | B2 | 6/2010 | Phillips et al. |
| 7,747,330 | B2 | 6/2010 | Nolan et al. |
| 7,771,838 | B1 | 8/2010 | He et al. |
| 7,774,069 | B2 | 8/2010 | Olson et al. |
| 7,801,619 | B2 | 9/2010 | Gerber et al. |
| 7,813,803 | B2 | 10/2010 | Heruth et al. |
| 7,813,809 | B2 | 10/2010 | Strother et al. |
| 7,826,901 | B2 | 11/2010 | Lee et al. |
| 7,848,818 | B2 | 12/2010 | Barolat et al. |
| 7,904,167 | B2 | 3/2011 | Klosterman et al. |
| 7,912,555 | B2 | 3/2011 | Swoyer et al. |
| 7,925,357 | B2 | 4/2011 | Phillips et al. |
| 7,932,696 | B2 | 4/2011 | Peterson |
| 7,933,656 | B2 | 4/2011 | Sieracki et al. |
| 7,935,051 | B2 | 5/2011 | Miles et al. |
| 7,937,158 | B2 | 5/2011 | Erickson et al. |
| 7,952,349 | B2 | 5/2011 | Huang et al. |
| 7,957,818 | B2 | 6/2011 | Swoyer |
| 7,979,119 | B2 | 7/2011 | Kothandaraman et al. |
| 7,979,126 | B2 | 7/2011 | Payne et al. |

(56) References Cited

U.S. PATENT DOCUMENTS

| | | | |
|---|---|---|---|
| 7,988,507 B2 | 8/2011 | Darley et al. | |
| 8,000,782 B2 | 8/2011 | Gharib et al. | |
| 8,000,805 B2 | 8/2011 | Swoyer et al. | |
| 8,005,535 B2 | 8/2011 | Gharib et al. | |
| 8,005,549 B2 | 8/2011 | Boser et al. | |
| 8,005,550 B2 | 8/2011 | Boser et al. | |
| 8,019,423 B2 | 9/2011 | Possover | |
| 8,019,443 B2 * | 9/2011 | Schleicher | A61N 1/0558 607/117 |
| 8,024,047 B2 | 9/2011 | Olson et al. | |
| 8,036,756 B2 | 10/2011 | Swoyer et al. | |
| 8,044,635 B2 | 10/2011 | Peterson | |
| 8,050,769 B2 | 11/2011 | Gharib et al. | |
| 8,055,337 B2 | 11/2011 | Moffitt et al. | |
| 8,068,912 B2 | 11/2011 | Kaula et al. | |
| 8,083,663 B2 | 12/2011 | Gross et al. | |
| 8,103,360 B2 | 1/2012 | Foster | |
| 8,116,862 B2 | 2/2012 | Stevenson et al. | |
| 8,121,701 B2 | 2/2012 | Woods et al. | |
| 8,129,942 B2 | 3/2012 | Park et al. | |
| 8,131,358 B2 | 3/2012 | Moffitt et al. | |
| 8,140,168 B2 | 3/2012 | Olson et al. | |
| 8,145,324 B1 | 3/2012 | Stevenson et al. | |
| 8,150,530 B2 | 4/2012 | Wesselink | |
| 8,175,717 B2 | 5/2012 | Haller et al. | |
| 8,180,451 B2 | 5/2012 | Hickman et al. | |
| 8,180,452 B2 | 5/2012 | Shaquer | |
| 8,180,461 B2 | 5/2012 | Mamo et al. | |
| 8,214,042 B2 | 7/2012 | Ozawa et al. | |
| 8,214,048 B1 | 7/2012 | Whitehurst et al. | |
| 8,214,051 B2 | 7/2012 | Sieracki et al. | |
| 8,219,196 B2 | 7/2012 | Torgerson | |
| 8,219,202 B2 | 7/2012 | Giftakis et al. | |
| 8,233,990 B2 | 7/2012 | Goetz | |
| 8,255,057 B2 | 8/2012 | Fang et al. | |
| 8,311,636 B2 | 11/2012 | Gerber et al. | |
| 8,314,594 B2 | 11/2012 | Scott et al. | |
| 8,332,040 B1 | 12/2012 | Winstrom | |
| 8,340,786 B2 | 12/2012 | Gross et al. | |
| 8,362,742 B2 | 1/2013 | Kallmyer | |
| 8,369,943 B2 | 2/2013 | Shuros et al. | |
| 8,386,048 B2 | 2/2013 | McClure et al. | |
| 8,417,346 B2 | 4/2013 | Giftakis et al. | |
| 8,423,146 B2 | 4/2013 | Giftakis et al. | |
| 8,447,402 B1 | 5/2013 | Jiang et al. | |
| 8,447,408 B2 | 5/2013 | North et al. | |
| 8,457,756 B2 | 6/2013 | Rahman | |
| 8,457,758 B2 | 6/2013 | Olson et al. | |
| 8,480,437 B2 | 7/2013 | Dilmaghanian et al. | |
| 8,494,625 B2 | 7/2013 | Hargrove | |
| 8,515,545 B2 | 8/2013 | Trier | |
| 8,538,530 B1 | 9/2013 | Orinski | |
| 8,543,223 B2 | 9/2013 | Sage et al. | |
| 8,549,015 B2 | 10/2013 | Barolat | |
| 8,554,322 B2 | 10/2013 | Olson et al. | |
| 8,555,894 B2 | 10/2013 | Schulman et al. | |
| 8,562,539 B2 | 10/2013 | Marino | |
| 8,571,677 B2 | 10/2013 | Torgerson et al. | |
| 8,577,474 B2 | 11/2013 | Rahman et al. | |
| 8,588,917 B2 | 11/2013 | Whitehurst et al. | |
| 8,626,314 B2 | 1/2014 | Swoyer et al. | |
| 8,644,933 B2 | 2/2014 | Ozawa et al. | |
| 8,655,451 B2 | 2/2014 | Klosterman et al. | |
| 8,700,175 B2 | 4/2014 | Fell | |
| 8,725,269 B2 | 5/2014 | Nolan et al. | |
| 8,738,141 B2 | 5/2014 | Smith et al. | |
| 8,738,148 B2 | 5/2014 | Olson et al. | |
| 8,750,985 B2 | 6/2014 | Parramon et al. | |
| 8,761,897 B2 | 6/2014 | Kaula et al. | |
| 8,768,452 B2 | 7/2014 | Gerber | |
| 8,774,912 B2 | 7/2014 | Gerber | |
| 8,954,148 B2 | 2/2015 | Labbe et al. | |
| 8,989,861 B2 | 3/2015 | Su et al. | |
| 9,089,712 B2 | 7/2015 | Joshi et al. | |
| 9,108,063 B2 | 8/2015 | Olson et al. | |
| 2003/0028231 A1 | 2/2003 | Partridge et al. | |
| 2004/0172115 A1 | 9/2004 | Miazga et al. | |
| 2004/0230282 A1 | 11/2004 | Cates et al. | |
| 2005/0104577 A1 | 5/2005 | Matei et al. | |
| 2006/0041295 A1 | 2/2006 | Osypka | |
| 2006/0074412 A1 * | 4/2006 | Zerfas | A61B 18/1477 606/41 |
| 2006/0095078 A1 * | 5/2006 | Tronnes | A61N 1/0558 607/2 |
| 2006/0142822 A1 | 6/2006 | Tulgar | |
| 2006/0206166 A1 | 9/2006 | Weiner | |
| 2007/0255368 A1 * | 11/2007 | Bonde | A61N 1/0558 607/116 |
| 2007/0255369 A1 | 11/2007 | Bonde et al. | |
| 2007/0265675 A1 | 11/2007 | Lund et al. | |
| 2007/0293914 A1 | 12/2007 | Woods et al. | |
| 2008/0103570 A1 * | 5/2008 | Gerber | A61N 1/0529 607/115 |
| 2008/0161874 A1 | 7/2008 | Bennett et al. | |
| 2008/0183236 A1 | 7/2008 | Gerber | |
| 2009/0012592 A1 * | 1/2009 | Buysman | A61N 1/05 607/116 |
| 2010/0076254 A1 | 3/2010 | Jimenez et al. | |
| 2010/0076534 A1 | 3/2010 | Mock | |
| 2010/0160997 A1 | 6/2010 | Johnson et al. | |
| 2010/0256696 A1 | 10/2010 | Schleicher et al. | |
| 2011/0251662 A1 | 10/2011 | Griswold et al. | |
| 2011/0270269 A1 | 11/2011 | Swoyer et al. | |
| 2011/0282416 A1 | 11/2011 | Hamann et al. | |
| 2011/0301667 A1 | 12/2011 | Olson et al. | |
| 2011/0313427 A1 | 12/2011 | Gindele et al. | |
| 2012/0041512 A1 | 2/2012 | Weiner | |
| 2012/0046712 A1 | 2/2012 | Woods et al. | |
| 2012/0053665 A1 | 3/2012 | Stolz et al. | |
| 2012/0095478 A1 | 4/2012 | Wang et al. | |
| 2012/0130448 A1 | 5/2012 | Woods et al. | |
| 2012/0191169 A1 | 7/2012 | Rothstein et al. | |
| 2012/0203320 A1 | 8/2012 | DiGiore et al. | |
| 2012/0276854 A1 | 11/2012 | Joshi et al. | |
| 2012/0276856 A1 | 11/2012 | Joshi et al. | |
| 2012/0310317 A1 | 12/2012 | Lund et al. | |
| 2013/0004925 A1 | 1/2013 | Labbe et al. | |
| 2013/0006330 A1 | 1/2013 | Wilder et al. | |
| 2013/0006331 A1 | 1/2013 | Weisgarber et al. | |
| 2013/0018447 A1 | 1/2013 | Ollivier et al. | |
| 2013/0131766 A1 | 5/2013 | Crosby et al. | |
| 2013/0150925 A1 | 6/2013 | Vamos et al. | |
| 2013/0150936 A1 | 6/2013 | Takahashi | |
| 2013/0150939 A1 | 6/2013 | Burnes et al. | |
| 2013/0184773 A1 | 7/2013 | Libbus et al. | |
| 2013/0197608 A1 | 8/2013 | Eiger | |
| 2013/0207863 A1 | 8/2013 | Joshi | |
| 2013/0310894 A1 | 11/2013 | Trier | |
| 2013/0331909 A1 | 12/2013 | Gerber | |
| 2014/0222112 A1 | 8/2014 | Fell | |
| 2014/0237806 A1 | 8/2014 | Smith et al. | |
| 2014/0277270 A1 | 9/2014 | Parramon et al. | |
| 2015/0214604 A1 | 7/2015 | Zhao et al. | |
| 2016/0045724 A1 * | 2/2016 | Lee | A61N 1/0558 604/20 |

FOREIGN PATENT DOCUMENTS

| | | |
|---|---|---|
| EP | 2243509 A1 | 10/2010 |
| WO | WO 98/20933 A1 | 5/1998 |
| WO | WO 00/56677 A1 | 3/2000 |
| WO | WO 00/27469 A2 | 5/2000 |
| WO | WO 03/084433 A3 | 10/2003 |
| WO | WO 2006/116205 A1 | 11/2006 |
| WO | WO 2007/022180 A1 | 2/2007 |
| WO | WO 2008/021524 A2 | 2/2008 |
| WO | WO 2008/153726 A2 | 12/2008 |
| WO | WO 2009/102536 A1 | 8/2009 |
| WO | WO 2009/135075 A1 | 11/2009 |
| WO | WO 2010/107751 A2 | 9/2010 |
| WO | WO 2011/059565 A1 | 5/2011 |
| WO | WO 2013/063798 A1 | 5/2013 |

(56) References Cited

FOREIGN PATENT DOCUMENTS

WO WO 2013/070490 A1 5/2013
WO WO 2013/156038 A1 10/2013

OTHER PUBLICATIONS

Chartier-Kastler, E., Sacral neuromodulation for treating the symptoms of overactive bladder syndrome and non-obstructive urinary retention:> 10 years of clincial experience, Journal Compilation, BJU International, 2007,101, pp. 417-423.
Ghovanloo, M., et al., A Small Size Large Voltage Compliance Programmable Current Source for Biomedical Implantable Microstimulators, Proceedings of the 25th Annual International Conference of the IEEE EMBS, Sep. 17-21, 2003, pp. 1979-1982.
Tanagho, E., et al., Bladder Pacemaker: Scientific Basis and Clinical Future, Urology, Dec. 1982, vol. 20, No. 6, pp. 614-619.

U.S. Appl. No. 14/827,081, filed Aug. 14, 2015.
U.S. Appl. No. 14/827,108, filed Aug. 14, 2015.
U.S. Appl. No. 14/991,752, filed Jan. 8, 2016.
U.S. Appl. No. 14/827,095, filed Aug. 14, 2015.
U.S. Appl. No. 14/827,067, filed Aug. 14, 2015.
U.S. Appl. No. 14/991,784, filed Jan. 8, 2016.
U.S. Appl. No. 62/101,888, filed Jan. 9, 2015.
U.S. Appl. No. 62/101,899, filed Jan. 9, 2015.
U.S. Appl. No. 62/041,611, filed Aug. 25, 2014.
U.S. Appl. No. 62/038,131, filed Aug. 15, 2014.
U.S. Appl. No. 62/101,897, filed Jan. 9, 2015.
U.S. Appl. No. 62/101,666, filed Jan. 9, 2015.
U.S. Appl. No. 62/101,884, filed Jan. 9, 2015.
U.S. Appl. No. 62/101,782, filed Jan. 9, 2015.
U.S. Appl. No. 62/191,134, filed Jul. 10, 2015.

\* cited by examiner

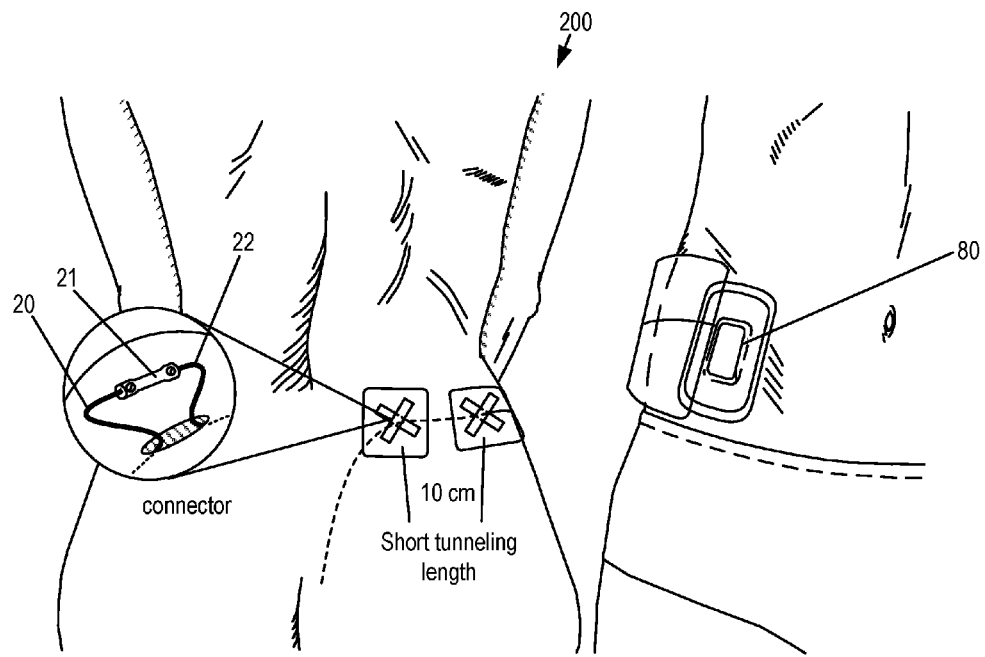
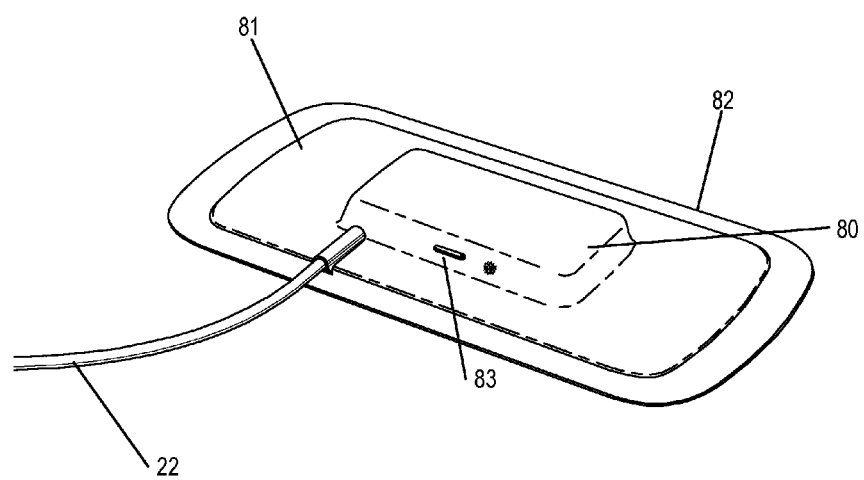
FIG. 3B

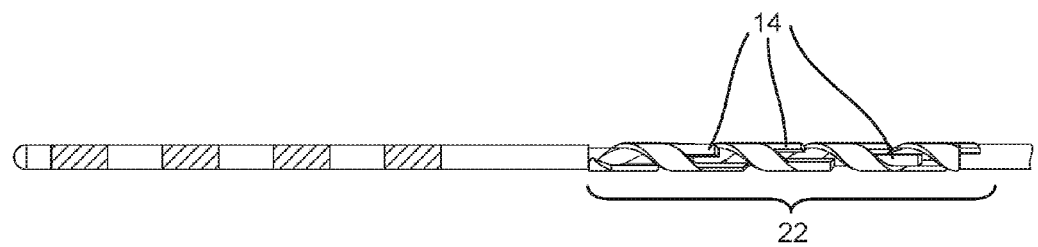
FIG. 9A
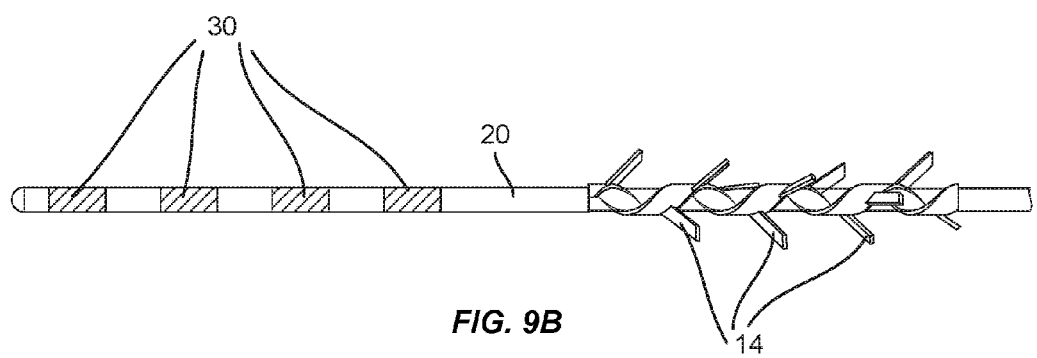
FIG. 9B
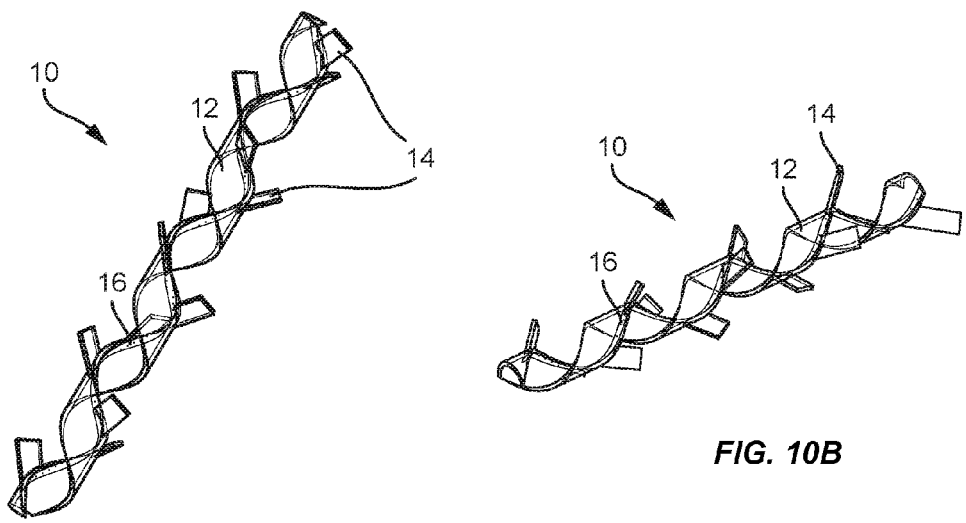
FIG. 10A
FIG. 10B

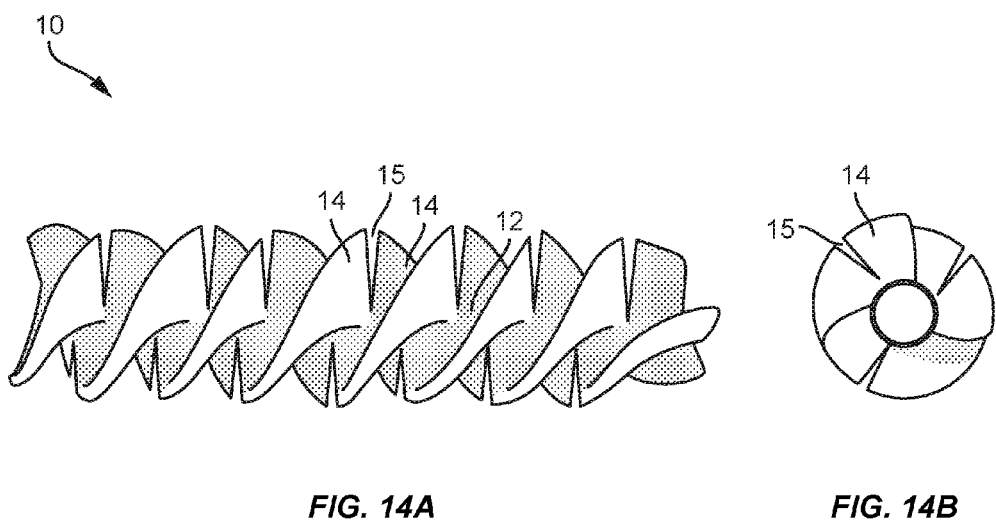
FIG. 14A  FIG. 14B

LASER CUT

RE-FLOW AFTER LASER CUT

IMPLANTABLE LEAD AFFIXATION STRUCTURE FOR NERVE STIMULATION TO ALLEVIATE BLADDER DYSFUNCTION AND OTHER INDICATION

CROSS-REFERENCES TO RELATED APPLICATIONS

The present application is a continuation of U.S. application Ser. No. 14/827,074, entitled "IMPLANTABLE LEAD AFFIXATION STRUCTURE FOR NERVE STIMULATION TO ALLEVIATE BLADDER DYSFUNCTION AND OTHER INDICATIONS," filed on Aug. 14, 2015, which claims the benefit of priority of U.S. Provisional Application No. 62/038,122 filed on Aug. 15, 2014 and U.S. Provisional Application No. 62/110,274 filed on Jan. 30, 2015; each of which is incorporated herein by reference in its entirety.

The present application is also related to U.S. Non-Provisional patent application Ser. No. 14/827,081, entitled "External Pulse Generator Device and Associated Methods for Trial Nerve Stimulation;" U.S. Non-Provisional patent application Ser. No. 14/827,108, entitled "Electromyographic Lead Positioning and Stimulation Titration in a Nerve Stimulation System for Treatment of Overactive Bladder;" U.S. Non-Provisional patent application Ser. No. 14/827,095, entitled "Integrated Electromyographic Clinician Programmer For Use With an Implantable Neurostimulator;" and U.S. Non-Provisional patent application Ser. No. 14/827,067, entitled "Systems and Methods for Neurostimulation Electrode Configurations Based on Neural Localization;" and U.S. Provisional Application Nos. 62/101,666, entitled "Patient Remote and Associated Methods of Use With a Nerve Stimulation System" filed on Jan. 9, 2015; 62/101,884, entitled "Attachment Devices and Associated Methods of Use With a Nerve Stimulation Charging Device" filed on Jan. 9, 2015; 62/101,782, entitled "Improved Antenna and Methods of Use For an Implantable Nerve Stimulator" filed on Jan. 9, 2015; and 62/191,134, entitled "Implantable Nerve Stimulator Having Internal Electronics Without ASIC and Methods of Use" filed on Jul. 10, 2015; each of which is assigned to the same assignee and incorporated herein by reference in its entirety for all purposes.

FIELD OF THE INVENTION

The present invention relates to neurostimulation treatment systems and associated devices, as well as methods of treatment, implantation and configuration of such treatment systems.

BACKGROUND OF THE INVENTION

Treatments with implantable neurostimulation systems have become increasingly common in recent years. While such systems have shown promise in treating a number of conditions, effectiveness of treatment may vary considerably between patients. A number of factors may lead to the very different outcomes that patients experience, and viability of treatment can be difficult to determine before implantation. For example, stimulation systems often make use of an array of electrodes to treat one or more target nerve structures. The electrodes are often mounted together on a multi-electrode lead, and the lead implanted in tissue of the patient at a position that is intended to result in electrical coupling of the electrode to the target nerve structure, typically with at least a portion of the coupling being provided via intermediate tissues. Other approaches may also be employed, for example, with one or more electrodes attached to the skin overlying the target nerve structures, implanted in cuffs around a target nerve, or the like. Regardless, the physician will typically seek to establish an appropriate treatment protocol by varying the electrical stimulation that is applied to the electrodes.

Current stimulation electrode placement/implantation techniques and known treatment setting techniques suffer from significant disadvantages. The nerve tissue structures of different patients can be quite different, with the locations and branching of nerves that perform specific functions and/or enervate specific organs being challenging to accurately predict or identify. The electrical properties of the tissue structures surrounding a target nerve structure may also be quite different among different patients, and the neural response to stimulation may be markedly dissimilar, with an electrical stimulation pulse pattern, pulse width, frequency, and/or amplitude that is effective to affect a body function of one patient and potentially imposing significant discomfort or pain, or having limited effect, on another patient. Even in patients where implantation of a neurostimulation system provides effective treatment, frequent adjustments and changes to the stimulation protocol are often required before a suitable treatment program can be determined, often involving repeated office visits and significant discomfort for the patient before efficacy is achieved. While a number of complex and sophisticated lead structures and stimulation setting protocols have been implemented to seek to overcome these challenges, the variability in lead placement results, the clinician time to establish suitable stimulation signals, and the discomfort (and in cases the significant pain) that is imposed on the patient remain less than ideal. In addition, the lifetime and battery life of such devices is relatively short, such that implanted systems are routinely replaced every few years, which requires additional surgeries, patient discomfort, and significant costs to healthcare systems.

Furthermore, since the morphology of the nerve structures vary considerably between patients, placement and alignment of neurostimulation leads relative the targeted nerve structures can be difficult to control, which can lead to inconsistent placement, unpredictable results and widely varying patient outcomes. For these reasons, neurostimulation leads typically include multiple electrodes with the hope that at least one electrode or a pair of electrodes will be disposed in a location suitable for delivering neurostimulation. One drawback with this approach is that repeated office visits may be required to determine the appropriate electrodes to use and/or to arrive at a neurostimulation program that delivers effective treatment. Often, the number of usable neurostimulation programs may be limited by imprecise lead placement.

The tremendous benefits of these neural stimulation therapies have not yet been fully realized. Therefore, it is desirable to provide improved neurostimulation methods, systems and devices, as well as methods for implanting such neurostimulation systems for a particular patient or condition being treated. It would be particularly helpful to provide such systems and methods so as to improve ease of use by the physician in positioning and affixation of such leads to ensure proper lead placement is maintained after implantation so as to provide consistent and predictable results upon delivery of neurostimulation therapy. Therefore, it is desirable to provide methods and devices for implanting neurostimulation leads that improve anchoring of the lead and allow for reduced delivery profile of the lead during implantation.

BRIEF SUMMARY OF THE INVENTION

The present invention relates to implantable neurostimulation systems, and in particular to devices and methods for anchoring implanted neurostimulation leads. In one aspect, the invention includes an anchoring body extending helically about the lead and a plurality of tines disposed along the anchoring body. The plurality of tines are biased toward a deployed position in which the tines extend laterally outward from the helical body so as to engage tissue sufficiently to inhibit axial displacement of the implanted lead. The tines are constructed so as to be resiliently deflectable toward the helical body during implantation so as to fold inward toward the helical anchoring body when constrained by a delivery sheath to facilitate delivery to the target location during implantation.

In one aspect, a neurostimulation system in accordance with aspect of the invention includes an implantable lead having one or more conductors disposed within a lead body, the one or more conductors extending from a proximal end of the lead to one or more neurostimulation electrodes disposed at or near a distal end of the lead; a pulse generator coupleable to the proximal end of the implantable lead, the pulse generator being electrically coupled with the one or more neurostimulation electrodes when coupled to the implantable lead, the pulse generator being configured to generate a plurality of electrical impulses for delivering a neurostimulation treatment to a patient through the one or more neurostimulation electrodes when implanted at a target location; and an anchor coupled with the lead body just proximal of the electrodes.

In one aspect, the anchor includes a helical body extending helically on the outside of the lead body along a longitudinal axis thereof and a plurality of tines extending laterally away from the helical body. Each of the plurality of tines is biased to a deployed configuration and a delivery configuration. In the deployed configuration, the plurality of tines extend laterally away from longitudinal axis when the helical body is disposed thereon, and in the delivery configuration, the plurality of tines are folded inward toward the longitudinal axis of the lead body to facilitate delivery of the neurostimulation lead during implantation. In certain embodiments, the anchor is configured such that, in the delivery configuration, each of the plurality of tines is folded against the lead body so as to further reduce the delivery profile and, in the delivery configuration, the anchor has a cross-section or crossing profile compatible with a sheath having a diameter of 5 French or higher. In certain embodiments, the helical body and the plurality of tines are integrally formed of the same material, while in other embodiments the tines may be separate elements attached to the helical body. The tines are formed of a material with sufficient stiffness so that engagement of tissue with the plurality of tines inhibits axial movement of the lead when implanted in a tissue of the patient at the target location. In some embodiments, the anchor may be molded from a polyurethane based material having a shore hardness within a range between 50A and 80D. In other embodiments, the anchor may be formed of a metal, such as a shape-memory alloy. In still other embodiments, the anchor may be formed of a combination of materials, such as a polymer based material and a metal, such as a shape-memory alloy wire.

In certain embodiments, the anchor is dimensioned so that the helical body extends a length between 10 mm to 30 mm along the lead body when coupled thereon, preferably about 20 mm. Each of the plurality of tines may extend laterally outward from the longitudinal axis a distance between 1 mm to 4 mm. Each of the plurality of tines may be between 1.5 mm to 3 mm in length and between 0.5 mm to 2.0 mm in width. In some embodiments, the plurality of tines include tines of varying length, width and angle in the proximal direction, while in other embodiments, the plurality of tines may be of differing lengths or may angle in both proximal and distal directions. The plurality of tines may have a generally rectangular tab shape and may include rounded or chamfered corners and/or edges so as to inhibit tissue damage at the corners and/or edges. In some embodiments, the tines are biased toward an angle between 30 to 80 degrees from the longitudinal axis in the deployed configuration.

In one aspect, the helical body attaches to the lead body in an anchoring portion having a recessed portion with a reduced profile so as to further reduce the cross section, such as to 2 mm or less so as to accommodate a 5 French sheath for use in implanting the lead. In some embodiments, the anchor includes multiple anchor sections that may be attached to one another and deployed adjacent one another. This feature may allow the user to customize the anchoring portion as to both length and tine direction of the anchor, by reverse the anchors or combining differing types of anchors within the anchoring portion. The anchor may further include one or more additional features, including any of: a radiopaque element extending a substantial length of the helical body so as to facilitate positioning using visualization techniques; an embedded shield material suitable for shielding magnetic resonance induced heating; and biodegradable or drug eluting tines.

In certain embodiments, the helical body is a continuous helical flap and the plurality of tines comprise a plurality of sections of the continuous helical flap, the plurality of section defined by a plurality of cuts along a length of the continuous helical flap so as to allow the plurality of sections to fold inward without overlapping one another.

In other embodiments, the anchor is formed by laser cutting a tubular portion of a material (e.g. polymer or metal, such as Nitinol) and setting the material while the anchor is in the deployed configuration by heat setting or reflow. In still other embodiments, the anchor may be formed by injection molding a polymer material in a multi-piece mold assembly, which allows for further variability in the anchor structure, such as varying thicknesses in different portions of the anchor.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

FIG. 3B shows an example of a neurostimulation system having a partly implanted stimulation lead and an external pulse generator adhered to the skin of the patient for use in a trial stimulation, in accordance with aspects of the invention.

FIGS. 9A-9B illustrate a neurostimulation lead with an anchor structure thereon before and after deployment, in accordance with aspects of the invention.

FIGS. 10A-10B illustrate an example anchor structure, in accordance with aspects of the invention.

FIGS. 14A-14B illustrate an example anchor structure, in accordance with aspects of the invention.

DETAILED DESCRIPTION OF THE INVENTION

Figure 1:
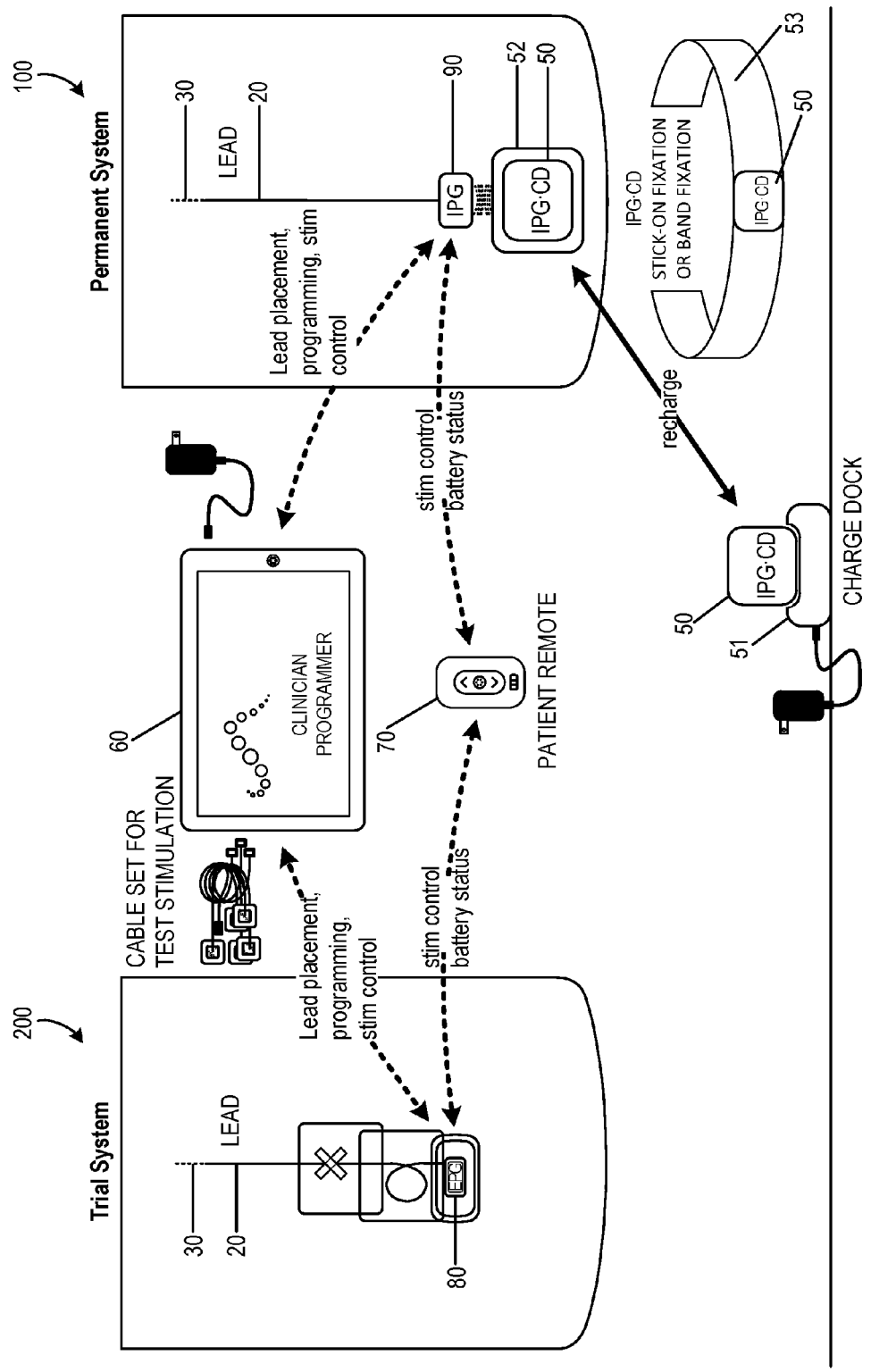
FIG. 1 schematically illustrates a nerve stimulation system, which includes a clinician programmer and a patient remote used in positioning and/or programming of both a trial neurostimulation system and a permanently implanted neurostimulation system, in accordance with aspects of the invention.

The present invention relates to neurostimulation treatment systems and associated devices, as well as methods of treatment, implantation/placement and configuration of such treatment systems. In particular embodiments, the invention relates to sacral nerve stimulation treatment systems configured to treat bladder dysfunctions, including overactive bladder ("OAB"), as well as fecal dysfunctions and relieve symptoms associated therewith. It will be appreciated however that the present invention may also be utilized for the treatment of pain or other indications, such as movement or affective disorders, as will be appreciated by one of skill in the art.

I. Neurostimulation Indications

Neurostimulation treatment systems, such as any of those described herein, can be used to treat a variety of ailments and associated symptoms, such as acute pain disorders, movement disorders, affective disorders, as well as bladder related dysfunction and bowel and fecal dysfunction. Examples of pain disorders that may be treated by neurostimulation include failed back surgery syndrome, reflex sympathetic dystrophy or complex regional pain syndrome, causalgia, arachnoiditis, and peripheral neuropathy. Movement orders include muscle paralysis, tremor, dystonia and Parkinson's disease. Affective disorders include depressions, obsessive-compulsive disorder, cluster headache, Tourette syndrome and certain types of chronic pain. Bladder related dysfunctions include but are not limited to OAB, urge incontinence, urgency-frequency, and urinary retention. OAB can include urge incontinence and urgency-frequency alone or in combination. Urge incontinence is the involuntary loss or urine associated with a sudden, strong desire to void (urgency). Urgency-frequency is the frequent, often uncontrollable urges to urinate (urgency) that often result in voiding in very small amounts (frequency). Urinary retention is the inability to empty the bladder. Neurostimulation treatments can be configured to address a particular condition by effecting neurostimulation of targeted nerve tissues relating to the sensory and/or motor control associated with that condition or associated symptom.

In one aspect, the methods and systems described herein are particularly suited for treatment of urinary and fecal dysfunctions. These conditions have been historically under-recognized and significantly underserved by the medical community. OAB is one of the most common urinary dysfunctions. It is a complex condition characterized by the presence of bothersome urinary symptoms, including urgency, frequency, nocturia and urge incontinence. It is estimated that about 40 million Americans suffer from OAB. Of the adult population, about 16% of all men and women live with OAB symptoms.

OAB symptoms can have a significant negative impact on the psychosocial functioning and the quality of life of patients. People with OAB often restrict activities and/or develop coping strategies. Furthermore, OAB imposes a significant financial burden on individuals, their families, and healthcare organizations. The prevalence of co-morbid conditions is also significantly higher for patients with OAB than in the general population. Co-morbidities may include falls and fractures, urinary tract infections, skin infections, vulvovaginitis, cardiovascular, and central nervous system pathologies. Chronic constipation, fecal incontinence, and overlapping chronic constipation occur more frequently in patients with OAB.

Conventional treatments of OAB generally include lifestyle modifications as a first course of action. Lifestyle modifications include eliminating bladder irritants (such as caffeine) from the diet, managing fluid intake, reducing weight, stopping smoking, and managing bowel regularity. Behavioral modifications include changing voiding habits (such as bladder training and delayed voiding), training pelvic floor muscles to improve strength and control of urethral sphincter, biofeedback and techniques for urge suppression. Medications are considered a second-line treatment for OAB. These include anti-cholinergic medications (oral, transdermal patch, and gel) and oral beta-3 adrenergic agonists. However, anti-cholinergics are frequently associated with bothersome, systemic side effects including dry mouth, constipation, urinary retention, blurred vision, somnolence, and confusion. Studies have found that more than 50% of patients stop using anti-cholinergic medications within 90 days due to a lack of benefit, adverse events, or cost.

When these approaches are unsuccessful, third-line treatment options suggested by the American Urological Association include intradetrusor (bladder smooth muscle) injections of botulinum toxin (BTX), Percutaneous Tibial Nerve Stimulation (PTNS) and Sacral Nerve Stimulation (SNM). BTX is administered via a series of intradetrusor injections under cystoscopic guidance, but repeat injections of BTX are generally required every 4 to 12 months to maintain effect and BTX may undesirably result in urinary retention. A number or randomized controlled studies have shown some efficacy of BTX injections in OAB patients, but long-term safety and effectiveness of BTX for OAB is largely unknown.

PTNS therapy consists of weekly, 30-minute sessions over a period of 12 weeks, each session using electrical stimulation that is delivered from a hand-held stimulator to the sacral plexus via the tibial nerve. For patients who respond well and continue treatment, ongoing sessions, typically every 3-4 weeks, are needed to maintain symptom reduction. There is potential for declining efficacy if patients fail to adhere to the treatment schedule. Efficacy of PTNS has been demonstrated in a few randomized-controlled studies, however, there is limited data on PTNS effectiveness beyond 3-years and PTNS is not recommended for patients seeking a cure for urge urinary incontinence (UUI) (e.g., 100% reduction in incontinence episodes) (EAU Guidelines).

II. Sacral Neuromodulation

SNM is an established therapy that provides a safe, effective, reversible, and long-lasting treatment option for the management of urge incontinence, urgency-frequency, and non-obstructive urinary retention. SNM therapy involves the use of mild electrical pulses to stimulate the sacral nerves located in the lower back. Electrodes are placed next to a sacral nerve, usually at the S3 level, by inserting the electrode leads into the corresponding foramen of the sacrum. The electrodes are inserted subcutaneously and are subsequently attached to an implantable pulse generator (IPG). The safety and effectiveness of SNM for the treatment of OAB, including durability at five years for both urge incontinence and urgency-frequency patients, is supported by multiple studies and is well-documented. SNM has also been approved to treat chronic fecal incontinence in patients who have failed or are not candidates for more conservative treatments.

A. Implantation of Sacral Neuromodulation System

Currently, SNM qualification has a trial phase, and is followed if successful by a permanent implant. The trial phase is a test stimulation period where the patient is allowed to evaluate whether the therapy is effective. Typically, there are two techniques that are utilized to perform the test stimulation. The first is an office-based procedure termed the Percutaneous Nerve Evaluation (PNE) and the other is a staged trial.

In the PNE, a foramen needle is typically used first to identify the optimal stimulation location, usually at the S3 level, and to evaluate the integrity of the sacral nerves. Motor and sensory responses are used to verify correct needle placement, as described in Table 1 below. A temporary stimulation lead (a unipolar electrode) is then placed near the sacral nerve under local anesthesia. This procedure can be performed in an office setting without fluoroscopy. The temporary lead is then connected to an external pulse generator (EPG) taped onto the skin of the patient during the trial phase. The stimulation level can be adjusted to provide an optimal comfort level for the particular patient. The patient will monitor his or her voiding for 3 to 7 days to see if there is any symptom improvement. The advantage of the PNE is that it is an incision free procedure that can be performed in the physician's office using local anesthesia. The disadvantage is that the temporary lead is not securely anchored in place and has the propensity to migrate away from the nerve with physical activity and thereby cause failure of the therapy. If a patient fails this trial test, the physician may still recommend the staged trial as described below. If the PNE trial is positive, the temporary trial lead is removed and a permanent quadri-polar tined lead is implanted along with an IPG under general anesthesia.

Figure 3A:
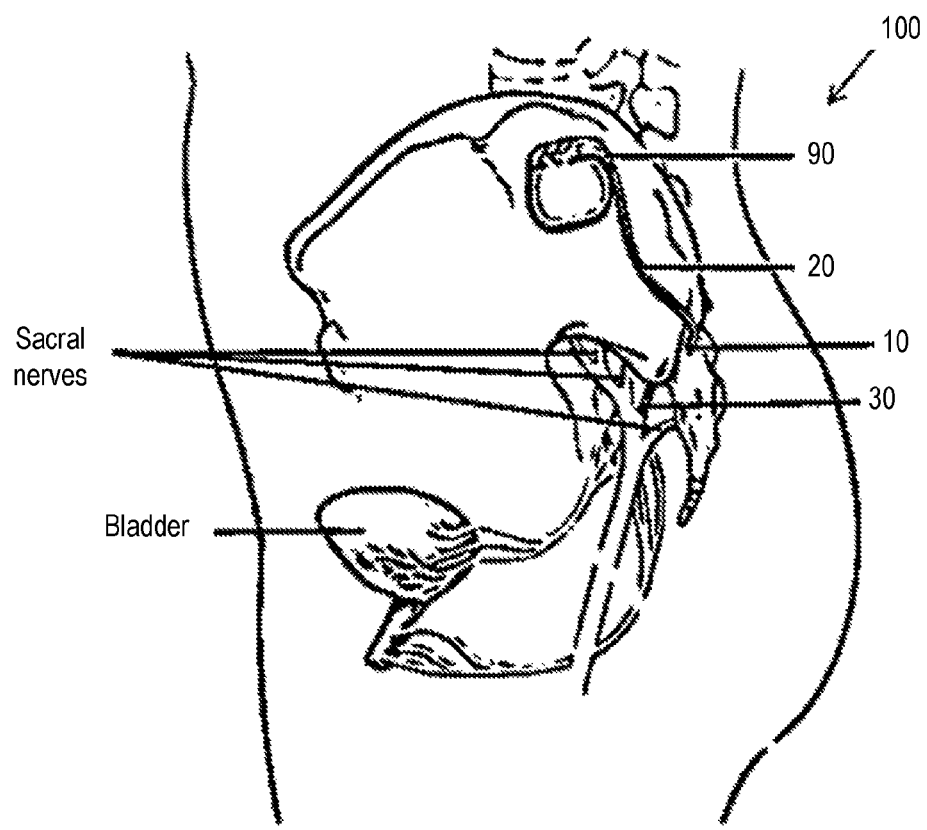
FIG. 3A shows an example of a fully implanted neurostimulation system in accordance with aspects of the invention.

A staged trial involves the implantation of the permanent quadri-polar tined stimulation lead into the patient from the start. It also requires the use of a foramen needle to identify the nerve and optimal stimulation location. The lead is implanted near the S3 sacral nerve and is connected to an EPG via a lead extension. This procedure is performed under fluoroscopic guidance in an operating room and under local or general anesthesia. The EPG is adjusted to provide an optimal comfort level for the patient and the patient monitors his or her voiding for up to two weeks. If the patient obtains meaningful symptom improvement, he or she is considered a suitable candidate for permanent implantation of the IPG under general anesthesia, typically in the upper buttock area, as shown in FIGS. 1 and 3A.

TABLE 1

Motor and Sensory Responses of SNM at Different Sacral Nerve Roots

| | Response | | |
|---|---|---|---|
| Nerve Innervation | Pelvic Floor | Foot/calf/leg | Sensation |
| S2 -Primary somatic contributor of pudendal nerve for external sphincter, leg, foot | "Clamp" * of anal sphincter | Leg/hip rotation, plantar flexion of entire foot, contraction of calf | Contraction of base of penis, vagina |
| S3 - Virtually all pelvic autonomic functions and striated mucle (levetor ani) | "bellows" ** of perineum | Plantar flexion of great toe, occasionally other toes | Pulling in rectum, extending forward to scrotum or labia |
| S4 - Pelvic autonomic and somatic; No leg pr foot | "bellows" ** | No lower extremity motor stimulation | Pulling in rectum only |

* Clamp: contraction of anal sphincter and, in males, retraction of base of penis. Move buttocks aside and look for anterior/posterior shortening of the perineal structures.
** Bellows: lifting and dropping of pelvic floor. Look for deepening and flattening of buttock groove In regard to measuring outcomes for SNM treatment of voiding dysfunction, the voiding dysfunction indications (e.g., urge incontinence, urgency-frequency, and non-obstructive urinary retention) are evaluated by unique primary voiding diary variables. The therapy outcomes are measured using these same variables. SNM therapy is considered successful if a minimum of 50% improvement occurs in any of primary voiding diary variables compared with the baseline. For urge incontinence patients, these voiding diary variables may include: number of leaking episodes per day, number of heavy leaking episodes per day, and number of pads used per day. For patients with urgency-frequency, primary voiding diary variables may include: number of voids per day, volume voided per void and degree of urgency experienced before each void. For patients with retention, primary voiding diary variables may include: catheterized volume per catheterization and number of catheterizations per day. For fecal incontinence patients, the outcome measures captured by the voiding diary include: number of leaking episodes per week, number of leaking days per week, and degree of urgency experienced before each leak.

The mechanism of action of SNM is multifactorial and impacts the neuro-axis at several different levels. In patients with OAB, it is believed that pudendal afferents can activate the inhibitory reflexes that promote bladder storage by inhibiting the afferent limb of an abnormal voiding reflex. This blocks input to the pontine micturition center, thereby restricting involuntary detrusor contractions without interfering with normal voiding patterns. For patients with urinary retention, SNM is believed to activate the pudendal nerve afferents originating from the pelvic organs into the spinal cord. At the level of the spinal cord, pudendal afferents may turn on voiding reflexes by suppressing exaggerated guarding reflexes, thus relieving symptoms of patients with urinary retention so normal voiding can be facilitated. In patients with fecal incontinence, it is hypothesized that SNM stimulates pudendal afferent somatic fibers that inhibit colonic propulsive activity and activates the internal anal sphincter, which in turn improves the symptoms of fecal incontinence patients.

The present invention relates to a system adapted to deliver neurostimulation to targeted nerve tissues in a manner that results in partial or complete activation of the target nerve fibers, causes the augmentation or inhibition of neural activity in nerves, potentially the same or different than the stimulation target, that control the organs and structures associated with bladder and bowel function.

B. EMG Assisted Neurostimulation Lead Placement and Programming

While conventional sacral nerve stimulation approaches have shown efficacy in treatment of bladder and bowel related dysfunctions, there exists a need to improve positioning of the neurostimulation leads and consistency between the trial and permanent implantation positions of the lead as well as to improve methods of programming. Neurostimulation relies on consistently delivering therapeutic stimulation from a pulse generator, via one or more neurostimulation electrodes, to particular nerves or targeted regions. The neurostimulation electrodes are provided on a distal end of an implantable lead that can be advanced through a tunnel formed in patient tissue. Implantable neurostimulation systems provide patients with great freedom and mobility, but it may be easier to adjust the neurostimulation electrodes of such systems before they are surgically implanted. It is desirable for the physician to confirm that the patient has desired motor and/or sensory responses before implanting an IPG. For at least some treatments (including treatments of at least some forms of urinary and/or fecal dysfunction), demonstrating appropriate motor responses may be highly beneficial for accurate and objective lead placement while the sensory response may not be required or not available (e.g., patient is under general anesthesia).

Placement and calibration of the neurostimulation electrodes and implantable leads sufficiently close to specific nerves can be beneficial for the efficacy of treatment. Accordingly, aspects and embodiments of the present disclosure are directed to aiding and refining the accuracy and precision of neurostimulation electrode placement. Further, aspects and embodiments of the present disclosure are directed to aiding and refining protocols for setting therapeutic treatment signal parameters for a stimulation program implemented through implanted neurostimulation electrodes.

Prior to implantation of the permanent device, patients may undergo an initial testing phase to estimate potential response to treatment. As discussed above, PNE may be done under local anesthesia, using a test needle to identify the appropriate sacral nerve(s) according to a subjective sensory response by the patient. Other testing procedures can involve a two-stage surgical procedure, where a quadripolar tined lead is implanted for a testing phase (Stage 1) to determine if patients show a sufficient reduction in symptom frequency, and if appropriate, proceeding to the permanent surgical implantation of a neuromodulation device. For testing phases and permanent implantation, determining the location of lead placement can be dependent on subjective qualitative analysis by either or both of a patient or a physician.

In exemplary embodiments, determination of whether or not an implantable lead and neurostimulation electrode is located in a desired or correct location can be accomplished through use of electromyography ("EMG"), also known as surface electromyography. EMG, is a technique that uses an EMG system or module to evaluate and record electrical activity produced by muscles, producing a record called an electromyogram. EMG detects the electrical potential generated by muscle cells when those cells are electrically or neurologically activated. The signals can be analyzed to detect activation level or recruitment order. EMG can be performed through the skin surface of a patient, intramuscularly or through electrodes disposed within a patient near target muscles, or using a combination of external and internal structures. When a muscle or nerve is stimulated by an electrode, EMG can be used to determine if the related muscle is activated, (i.e. whether the muscle fully contracts, partially contracts, or does not contract) in response to the stimulus. Accordingly, the degree of activation of a muscle can indicate whether an implantable lead or neurostimulation electrode is located in the desired or correct location on a patient. Further, the degree of activation of a muscle can indicate whether a neurostimulation electrode is providing a stimulus of sufficient strength, amplitude, frequency, or duration to affect a treatment regimen on a patient. Thus, use of EMG provides an objective and quantitative means by which to standardize placement of implantable leads and neurostimulation electrodes, reducing the subjective assessment of patient sensory responses.

In some approaches, positional titration procedures may optionally be based in part on a paresthesia or pain-based subjective response from a patient. In contrast, EMG triggers a measureable and discrete muscular reaction. As the efficacy of treatment often relies on precise placement of the neurostimulation electrodes at target tissue locations and the consistent, repeatable delivery of neurostimulation therapy, using an objective EMG measurement can substantially improve the utility and success of SNM treatment. The measureable muscular reaction can be a partial or a complete muscular contraction, including a response below the triggering of an observable motor response, such as those shown in Table 1, depending on the stimulation of the target muscle. In addition, by utilizing a trial system that allows the neurostimulation lead to remain implanted for use in the permanently implanted system, the efficacy and outcome of the permanently implanted system is more consistent with the results of the trial period, which moreover leads to improved patient outcomes.

C. Example System Embodiments

FIG. 1 schematically illustrates example nerve stimulation system setups, which includes a setup for use in a trial neurostimulation system 200 and a setup for use in a permanently implanted neurostimulation system 100, in accordance with aspects of the invention. The EPG 80 and IPG 50 are each compatible with and wirelessly communicate with a clinician programmer (CP) 60 and a patient remote 70, which are used in positioning and/or programming the trial neurostimulation system 200 and/or permanently implanted system 100 after a successful trial. As discussed above, the system utilizes a cable set and EMG sensor patches in the trial system setup 100 to facilitate lead placement and neurostimulation programming. CP can include specialized software, specialized hardware, and/or both, to aid in lead placement, programming, re-programming, stimulation control, and/or parameter setting. In addition, each of the IPG and the EPG allows the patient at least some control over stimulation (e.g., initiating a pre-set program, increasing or decreasing stimulation), and/or to monitor battery status with the patient remote. This approach also allows for an almost seamless transition between the trial system and the permanent system.

In one aspect, the CP 60 is used by a physician to adjust the settings of the EPG and/or IPG while the lead is implanted within the patient. The CP can be a tablet computer used by the clinician to program the IPG, or to control the EPG during the trial period. The CP can also include capability to record stimulation-induced electromyograms to facilitate lead placement and programming. The patient remote 70 can allow the patient to turn the stimulation on or off, or to vary stimulation from the IPG while implanted, or from the EPG during the trial phase.

In another aspect, the CP 60 has a control unit which can include a microprocessor and specialized computer-code instructions for implementing methods and systems for use by a physician in deploying the treatment system and setting up treatment parameters. The CP generally includes a graphical user interface, an EMG module, an EMG input that can couple to an EMG output stimulation cable, an EMG stimulation signal generator, and a stimulation power source. The stimulation cable can further be configured to couple to any or all of an access device (e.g., a foramen needle), a treatment lead of the system, or the like. The EMG input may be configured to be coupled with one or more sensory patch electrode(s) for attachment to the skin of the patient adjacent a muscle (e.g., a muscle enervated by a target nerve). Other connectors of the CP may be configured for coupling with an electrical ground or ground patch, an electrical pulse generator (e.g., an EPG or an IPG), or the like. As noted above, the CP can include a module with hardware and computer-code to execute EMG analysis, where the module can be a component of the control unit microprocessor, a pre-processing unit coupled to or in-line with the stimulation and/or sensory cables, or the like.

In other aspects, the CP 60 allows the clinician to read the impedance of each electrode contact whenever the lead is connected to an EPG, an IPG or a CP to ensure reliable connection is made and the lead is intact. This may be used as an initial step in both positioning the lead and in programming the leads to ensure the electrodes are properly functioning. The CP 60 is also able to save and display previous (e.g., up to the last four) programs that were used by a patient to help facilitate re-programming. In some embodiments, the CP 60 further includes a USB port for saving reports to a USB drive and a charging port. The CP is configured to operate in combination with an EPG when placing leads in a patient body as well with the IPG during programming. The CP can be electronically coupled to the EPG during test simulation through a specialized cable set or through wireless communication, thereby allowing the CP to configure, modify, or otherwise program the electrodes on the leads connected to the EPG. The CP may also include physical on/off buttons to turn the CP on and off and/or to turn stimulation on and off.

The electrical pulses generated by the EPG and IPG are delivered to one or more targeted nerves via one or more neurostimulation electrodes at or near a distal end of each of one or more leads. The leads can have a variety of shapes, can be a variety of sizes, and can be made from a variety of materials, which size, shape, and materials can be tailored to the specific treatment application. While in this embodiment, the lead is of a suitable size and length to extend from the IPG and through one of the foramen of the sacrum to a targeted sacral nerve, in various other applications, the leads may be, for example, implanted in a peripheral portion of the patient's body, such as in the arms or legs, and can be configured to deliver electrical pulses to the peripheral nerve such as may be used to relieve chronic pain. It is appreciated that the leads and/or the stimulation programs may vary according to the nerves being targeted.

Figure 2A:
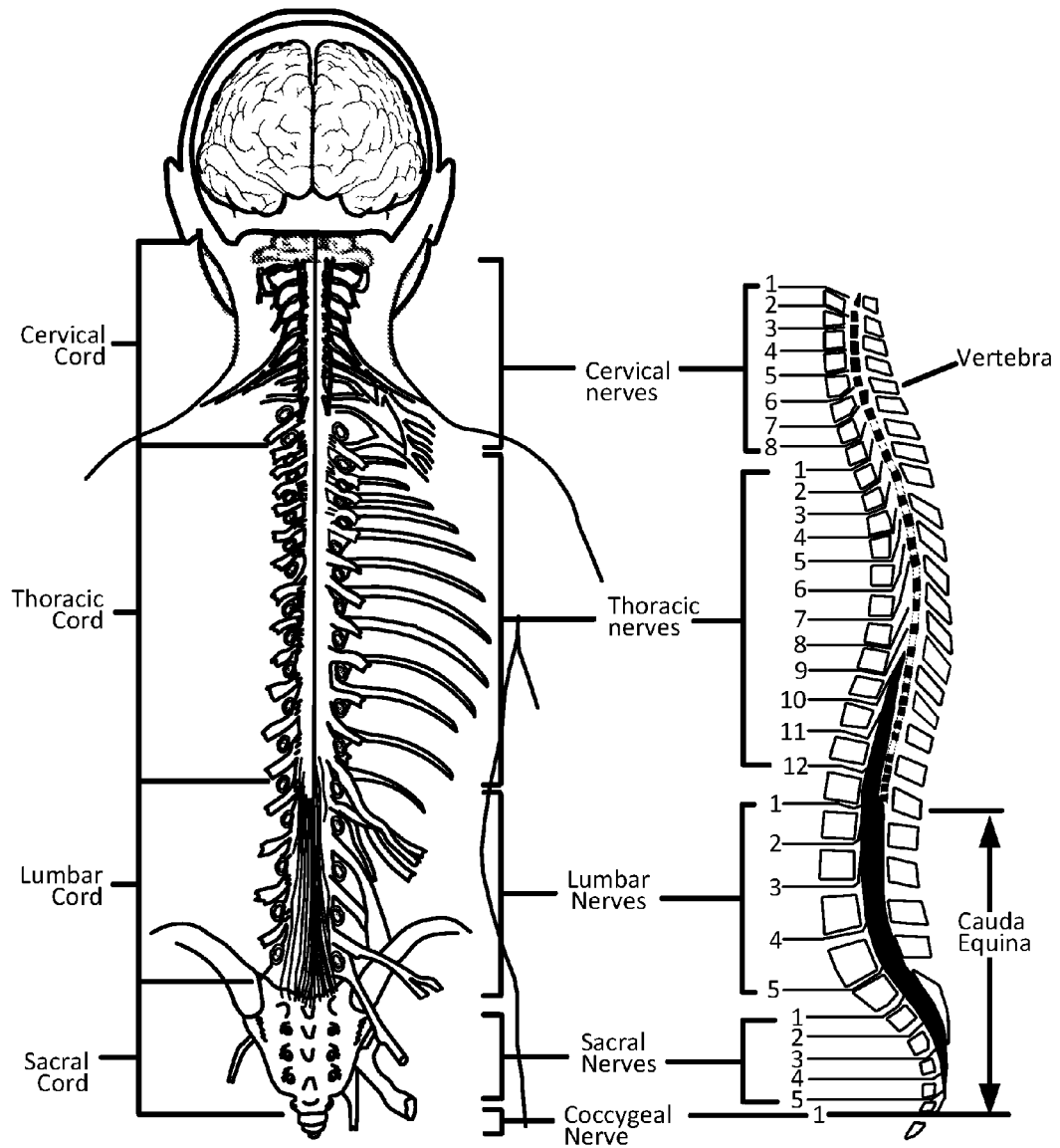
FIGS. 2A-2C show diagrams of the nerve structures along the spine, the lower back and sacrum region, which may be stimulated in accordance with aspects of the invention.
Figure 2B:
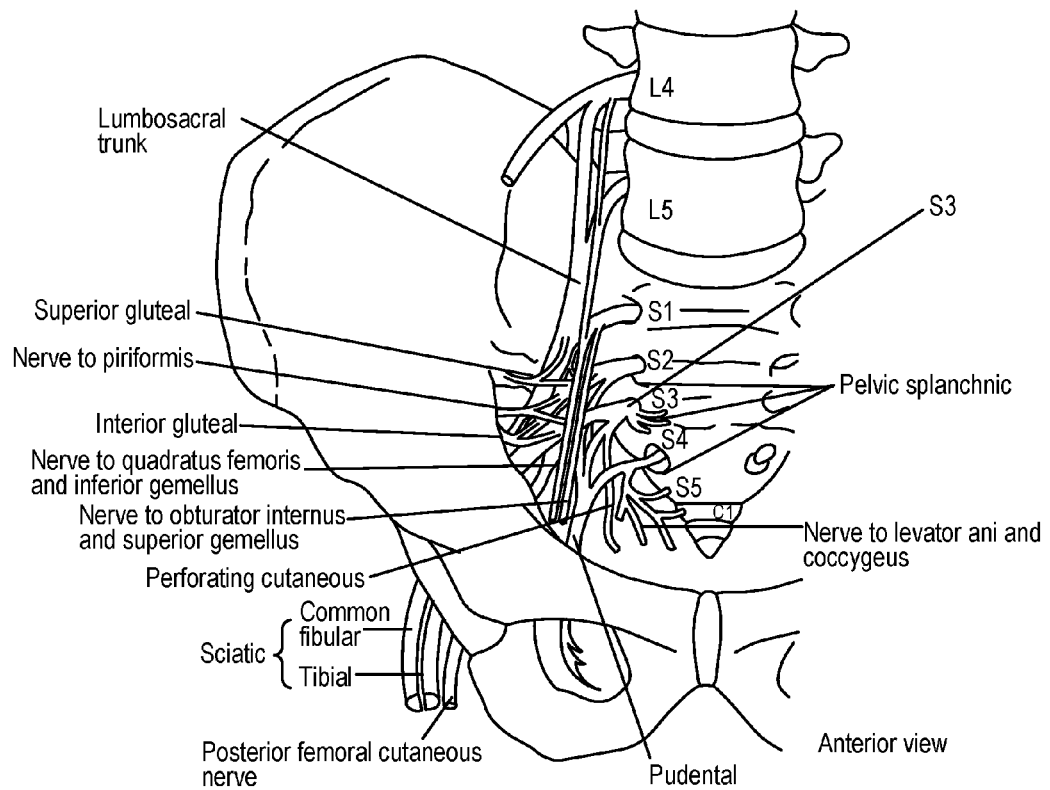
Figure 2C:
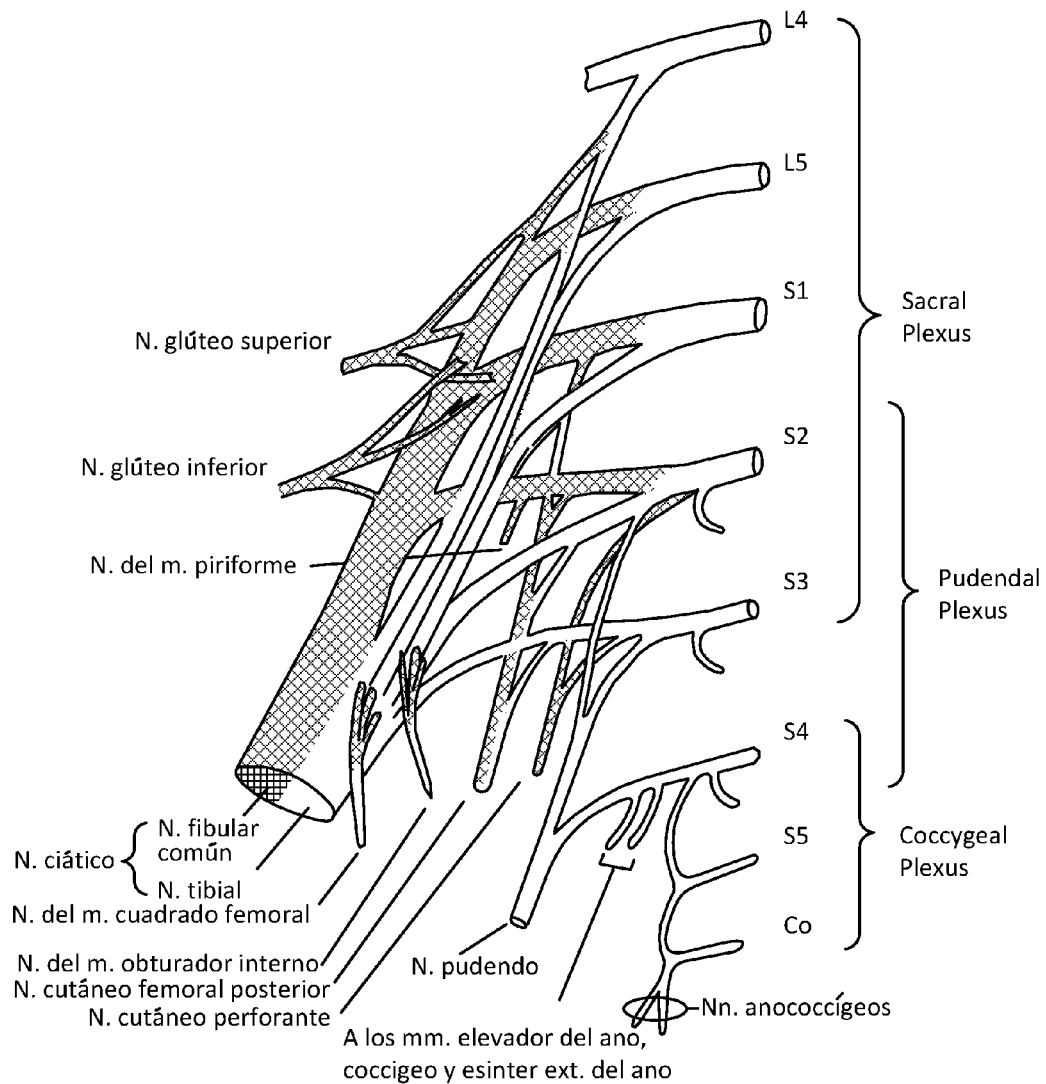

FIGS. 2A-2C show diagrams of various nerve structures of a patient, which may be used in neurostimulation treatments, in accordance with aspects of the invention. FIG. 2A shows the different sections of the spinal cord and the corresponding nerves within each section. The spinal cord is a long, thin bundle of nerves and support cells that extend from the brainstem along the cervical cord, through the thoracic cord and to the space between the first and second lumbar vertebra in the lumbar cord. Upon exiting the spinal cord, the nerve fibers split into multiple branches that innervate various muscles and organs transmitting impulses of sensation and control between the brain and the organs and muscles. Since certain nerves may include branches that innervate certain organs, such as the bladder, and branches that innervate certain muscles of the leg and foot, stimulation of the nerve at or near the nerve root near the spinal cord can stimulate the nerve branch that innervate the targeted organ, which may also result in muscle responses associated with the stimulation of the other nerve branch. Thus, by monitoring for certain muscle responses, such as those in Table 1, either visually, through the use of EMG as described herein or both, the physician can determine whether the targeted nerve is being stimulated. While stimulation at a certain level may evoke robust muscle responses visible to the naked eye, stimulation at a lower level (e.g. sub-threshold) may still provide activation of the nerve associated with the targeted organ while evoking no corresponding muscle response or a response only visible with EMG. In some embodiments, this low level stimulation also does not cause any paresthesia. This is advantageous as it allows for treatment of the condition by neurostimulation without otherwise causing patient discomfort, pain or undesired muscle responses.

FIG. 2B shows the nerves associated with the lower back section, in the lower lumbar cord region where the nerve bundles exit the spinal cord and travel through the sacral foramens of the sacrum. In some embodiments, the neurostimulation lead is advanced through the foramen until the neurostimulation electrodes are positioned at the anterior sacral nerve root, while the anchoring portion of the lead proximal of the stimulation electrodes are generally disposed dorsal of the sacral foramen through which the lead passes, so as to anchor the lead in position. FIG. 2C shows detail views of the nerves of the lumbosacral trunk and the sacral plexus, in particular, the S1-S5 nerves of the lower sacrum. The S3 sacral nerve is of particular interest for treatment of bladder related dysfunction, and in particular OAB.

FIG. 3A schematically illustrates an example of a fully implanted neurostimulation system 100 adapted for sacral nerve stimulation. Neurostimulation system 100 includes an IPG implanted in a lower back region and connected to a neurostimulation lead extending through the S3 foramen for stimulation of the S3 sacral nerve. The lead is anchored by a tined anchor portion 30 that maintains a position of a set of neurostimulation electrodes 40 along the targeted nerve, which in this example, is the anterior sacral nerve root S3 which enervates the bladder so as to provide therapy for various bladder related dysfunctions. While this embodiment is adapted for sacral nerve stimulation, it is appreciated that similar systems can be used in treating patients with, for example, chronic, severe, refractory neuropathic pain originating from peripheral nerves or various urinary dysfunctions or still further other indications. Implantable neurostimulation systems can be used to either stimulate a target peripheral nerve or the posterior epidural space of the spine.

Properties of the electrical pulses can be controlled via a controller of the implanted pulse generator. In some embodiments, these properties can include, for example, the frequency, amplitude, pattern, duration, or other aspects of the electrical pulses. These properties can include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In the embodiment depicted in FIG. 3A, the implantable neurostimulation system 100 includes a controller in the IPG having one or more pulse programs, plans, or patterns that may be pre-programmed or created as discussed above. In some embodiments, these same properties associated with the IPG may be used in an EPG of a partly implanted trial system used before implantation of the permanent neurostimulation system 100.

FIG. 3B shows a schematic illustration of a trial neurostimulation system 200 utilizing an EPG patch 81 adhered to the skin of a patient, particularly to the abdomen of a patient, the EPG 80 being encased within the patch. In one aspect, the lead is hardwired to the EPG, while in another the lead is removably coupled to the EPG through a port or aperture in the top surface of the flexible patch 81. Excess lead can be secured by an additional adherent patch. In one aspect, the EPG patch is disposable such that the lead can be disconnected and used in a permanently implanted system without removing the distal end of the lead from the target location. Alternatively, the entire system can be disposable and replaced with a permanent lead and IPG. When the lead of the trial system is implanted, an EMG obtained via the CP using one or more sensor patches can be used to ensure that the leads are placed at a location proximate to the target nerve or muscle, as discussed previously.

In some embodiments, the trial neurostimulation system utilizes an EPG 80 within an EPG patch 81 that is adhered to the skin of a patient and is coupled to the implanted neurostimulation lead 20 through a lead extension 22, which is coupled with the lead 20 through a connector 21. This extension and connector structure allows the lead to be extended so that the EPG patch can be placed on the abdomen and allows use of a lead having a length suitable for permanent implantation should the trial prove successful. This approach may utilize two percutaneous incisions, the connector provided in the first incision and the lead extensions extending through the second percutaneous incision, there being a short tunneling distance (e.g., about 10 cm) there between. This technique may also minimize movement of an implanted lead during conversion of the trial system to a permanently implanted system.

In one aspect, the EPG unit is wirelessly controlled by a patient remote and/or the CP in a similar or identical manner as the IPG of a permanently implanted system. The physician or patient may alter treatment provided by the EPG through use of such portable remotes or programmers and the treatments delivered are recorded on a memory of the programmer for use in determining a treatment suitable for use in a permanently implanted system. The CP can be used in lead placement, programming and/or stimulation control in each of the trial and permanent nerve stimulation systems. In addition, each nerve stimulation system allows the patient to control stimulation or monitor battery status with the patient remote. This configuration is advantageous as it allows for an almost seamless transition between the trial system and the permanent system. From the patient's viewpoint, the systems will operate in the same manner and be controlled in the same manner, such that the patient's subjective experience in using the trial system more closely matches what would be experienced in using the permanently implanted system. Thus, this configuration reduces any uncertainties the patient may have as to how the system will operate and be controlled such that the patient will be more likely to receive a trial system or a permanent system.

As shown in the detailed view of FIG. 3B, the EPG 80 is encased within a flexible laminated patch 81, which include an aperture or port through which the EPG 80 is connected to the lead extension 22. The patch may further an "on/off" button 83 with a molded tactile detail to allow the patient to turn the EPG on and/or off through the outside surface of the adherent patch 81. The underside of the patch 81 is covered with a skin-compatible adhesive 82 for continuous adhesion to a patient for the duration of the trial period. For example, a breathable strip having skin-compatible adhesive 82 would allow the EPG 80 to remain attached to the patient continuously during the trial, which may last over a week, typically two weeks to four weeks, or even longer.

While the above described systems provide considerable improvements in locating an optimal position of the lead and fine tuning lead placement and an optimal neurostimulation program is determined, it is imperative after the lead is successfully placed to ensure that the lead position is maintained over the course of therapy. Should the neurostimulation lead migrate, even a small axial distance, the electrodes may shift from the targeted nerve tissue such that the neurostimulation treatment may not delivery consistent results or no longer provide therapeutic effect without reprogramming or repositioning the lead.

In a fully implantable system, the pulse generator is implanted in the patient in an area having adequate size to comfortably contain the pulse generator, typically in a lower back region or lower abdominal region. Since the electrodes may need to be located a considerable distance from the implantable pulse generator, depending on the treatment or therapy being delivered, a neurostimulation lead is used to deliver the electrical pulses from the implanted pulse generator to the electrodes. While many such systems have proven effective, studies have shown that over time the neurostimulation lead may move, particularly when the lead extends through areas subject to movement. Such movement can dislocate the electrodes from the targeted location, such that the neurostimulation treatment becomes ineffective, requiring adjustment or replacement of the lead. Therefore, it is desirable to provide an anchoring device on the stimulation lead in such systems to inhibit movement of the lead and dislocation of the electrodes. While conventional neurostimulation has developed various anchoring mechanisms, such mechanisms often complicate the implantation procedure, undesirably increase the delivery profile of the lead, are difficult to replace or remove, or have proven ineffective.

Figure 4:
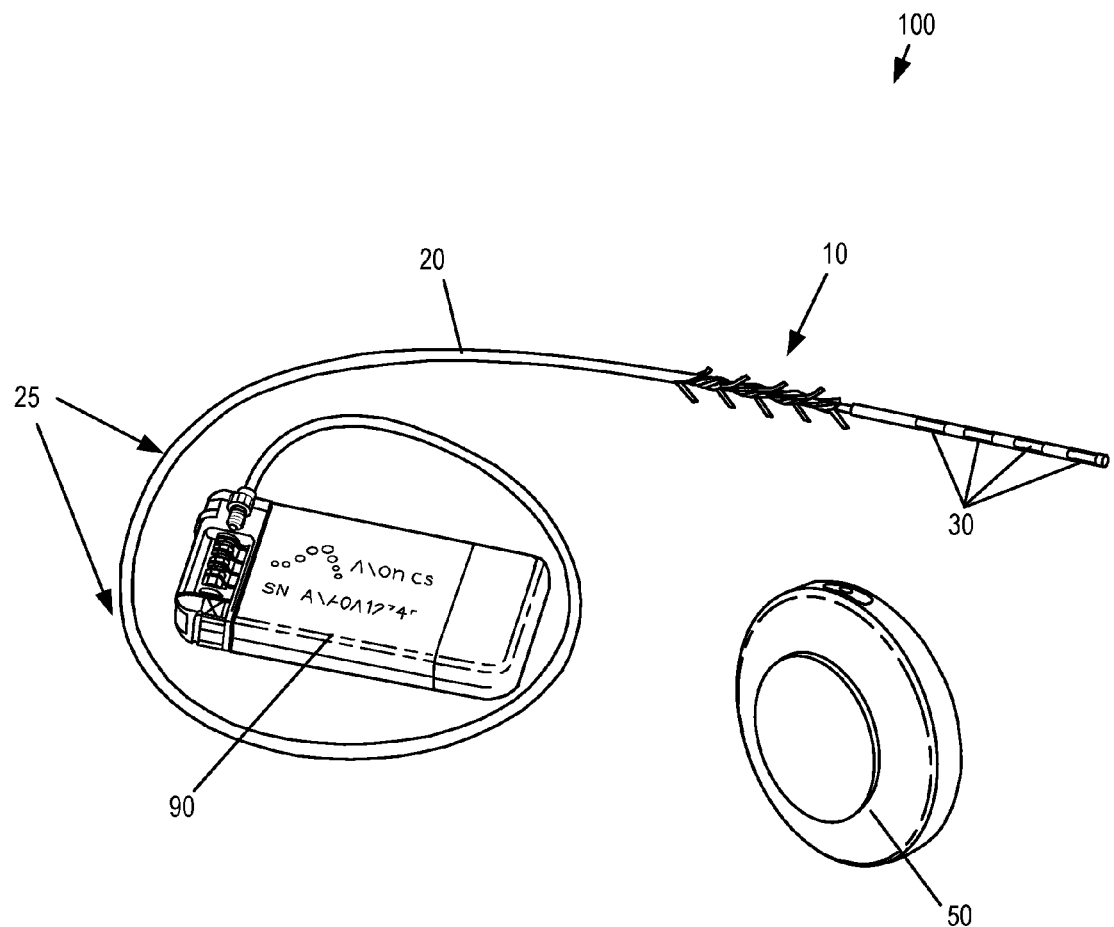
FIG. 4 shows an example of a neurostimulation system having an implantable stimulation lead, an implantable pulse generator, and an external charging device, in accordance with aspects of the invention.

FIG. 4 illustrates an example neurostimulation system 100 that is fully implantable and adapted for sacral nerve stimulation treatment. The implantable system 100 includes an IPG 90 that is coupled to a neurostimulation lead 20 that includes a group of neurostimulation electrodes 40 at a distal end of the lead. The lead includes a lead anchor portion 30 with a series of tines extending radially outward so as to anchor the lead and maintain a position of the neurostimulation lead 20 after implantation. The lead 20 may further include one or more radiopaque markers (e.g., silicon markers) 25 to assist in locating and positioning the lead using visualization techniques such as fluoroscopy. In some embodiments, the IPG provides monopolar or bipolar electrical pulses that are delivered to the targeted nerves through one or more neurostimulation electrodes. In sacral nerve stimulation, the lead is typically implanted through the S3 foramen as described herein.

As can be seen in FIG. 4, the neurostimulation lead 20 includes a plurality of neurostimulation electrodes 30 at a distal end of the lead and the anchor 10 is disposed just proximal of the electrodes 30. Typically, the anchor is disposed near and proximal of the plurality of electrodes so as to provide anchoring of the lead relatively close to the electrodes. This configuration is also advantageous as it allows for testing of the neurostimulation electrodes during implantation before deploying of the anchor (as described below), which allows the optimal location of the neurostimulation electrodes to be determined before the lead is anchored in place. As shown, the anchor 10 includes an anchor body 12 helically swept about the lead body and a plurality of tines 14 extending laterally outward from the helical body 12. This configuration is advantageous over conventional anchor devices as it provides a plurality of tines distributed both circumferentially and axially about the lead while extending from a common anchor body, thereby simplifying attachment and replacement of the anchoring tines. In addition, since the anchor body extends helically about the lead boy, this allows the flexibility of the lead body to be retained in the tined area. In one aspect, the anchor is constructed of a suitable material that is biocompatible as well as compatible with the material of which the lead body is formed and that is sufficiently flexible to provide anchoring force against the tissue without damaging the tissue.

Figure 5A:
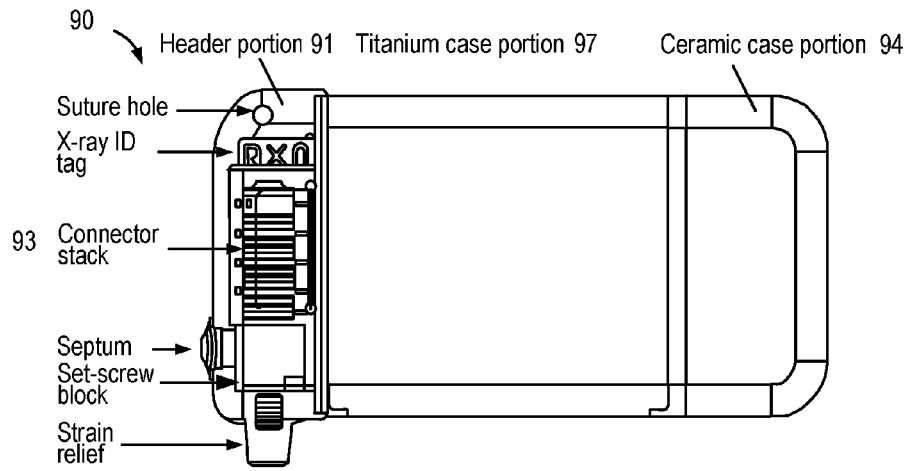
FIG. 5A-5C show detail views of an implantable pulse generator and associated components for use in a neurostimulation system, in accordance with aspects of the invention.
Figure 5B:
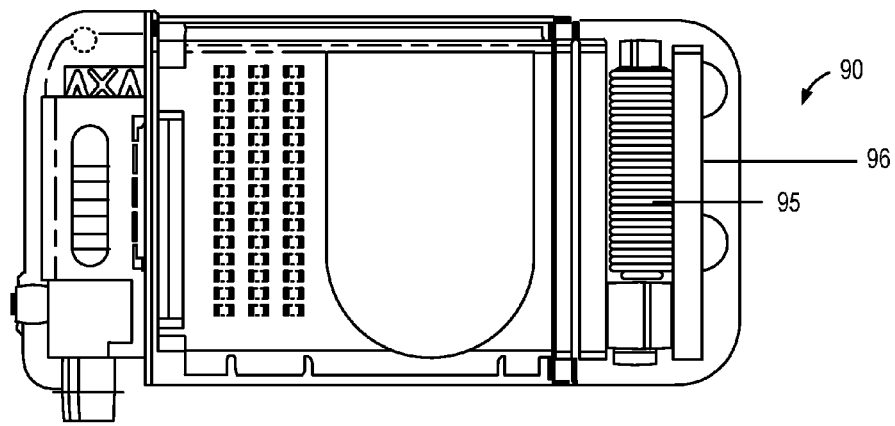
Figure 5C:
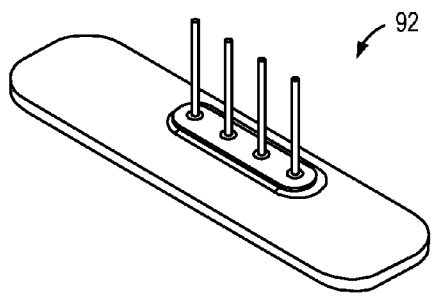

In one aspect, the IPG is rechargeable wirelessly through conductive coupling by use of a charging device 50 (CD), which is a portable device powered by a rechargeable battery to allow patient mobility while charging. The CD is used for transcutaneous charging of the IPG through RF induction. The CD can either be patched to the patient's skin using an adhesive or can be held in place using a belt 53 or by an adhesive patch 52, such as shown in the schematic of FIG. 1. The CD may be charged by plugging the CD directly into an outlet or by placing the CD in a charging dock or station 51 that connects to an AC wall outlet or other power source FIG. 5A-5C show detail views of the IPG and its internal components. In some embodiments, the pulse generator can generate one or more non-ablative electrical pulses that are delivered to a nerve to control pain or cause some other desired effect, for example to inhibit, prevent, or disrupt neural activity for the treatment of OAB or bladder related dysfunction. In some applications, the pulses having a pulse amplitude in a range between 0 mA to 1,000 mA, 0 mA to 100 mA, 0 mA to 50 mA, 0 mA to 25 mA, and/or any other or intermediate range of amplitudes may be used. One or more of the pulse generators can include a processor and/or memory adapted to provide instructions to and receive information from the other components of the implantable neurostimulation system. The processor can include a microprocessor, such as a commercially available microprocessor from Intel® or Advanced Micro Devices, Inc.®, or the like. An IPG may include an energy storage feature, such as one or more capacitors or a battery, one or more batteries, and typically includes a wireless charging unit.

One or more properties of the electrical pulses can be controlled via a controller of the IPG or EPG. In some embodiments, these properties can include, for example, the frequency, amplitude, pattern, duration, or other aspects of the timing and magnitude of the electrical pulses. These properties can further include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In one aspect, the IPG 90 includes a controller having one or more pulse programs, plans, or patterns that may be created and/or pre-programmed. In some embodiments, the IPG can be programmed to vary stimulation parameters including pulse amplitude in a range from 0 mA to 10 mA, pulse width in a range from 50 µs to 500 µs, pulse frequency in a range from 5 Hz to 250 Hz, stimulation modes (e.g., continuous or cycling), and electrode configuration (e.g., anode, cathode, or off), to achieve the optimal therapeutic outcome specific to the patient. In particular, this allows for an optimal setting to be determined for each patient even though each parameter may vary from person to person.

As shown in FIGS. 5A-5B, the IPG 90 may include a header portion 91 at one end and a ceramic portion 94 at the opposite end. The header portion 91 houses a feed through assembly 92 and connector stack 93, while the ceramic case portion 94 houses an antennae assembly 96 to facilitate wireless communication with the clinician program, the patient remote, and/or a charging coil to facilitate wireless charging with the CD. The remainder of the IPG is covered with a titanium case portion 97, which encases the printed circuit board, memory and controller components that facilitate the electrical pulse programs described above. In the example shown in FIG. 5C, the header portion of the IPG includes a four-pin feed-through assembly 92 that couples with the connector stack 93 in which the proximal end of the lead is coupled. The four pins correspond to the four electrodes of the neurostimulation lead. In some embodiments, a Balseal® connector block is electrically connected to four platinum/iridium alloy feed-through pins which are brazed to an alumina ceramic insulator plate along with a titanium alloy flange. This feed-through assembly is laser seam welded to a titanium-ceramic brazed case to form a complete hermetic housing for the electronics.

In the IPG shown in FIG. 5A, the ceramic and titanium brazed case is utilized on one end of the IPG where the ferrite coil and PCB antenna assemblies are positioned. A reliable hermetic seal is provided via a ceramic-to-metal brazing technique. The zirconia ceramic may comprise a 3Y-TZP (3 mol percent Yttria-stabilized tetragonal Zirconia Polycrystals) ceramic, which has a high flexural strength and impact resistance and has been commercially utilized in a number of implantable medical technologies. It will be appreciated, however, that other ceramics or other suitable materials may be used for construction of the IPG.

Utilization of ceramic material provides an efficient, radio-frequency-transparent window for wireless communication with the external patient remote and clinician's programmer as the communication antenna is housed inside the hermetic ceramic case. This ceramic window has further facilitated miniaturization of the implant while maintaining an efficient, radio-frequency-transparent window for long term and reliable wireless communication between the IPG and external controllers, such as the patient remote and CP. The IPG's wireless communication is generally stable over the lifetime of the device, unlike prior art products where the communication antenna is placed in the header outside the hermetic case. The communication reliability of such prior art devices tends to degrade due to the change in dielectric constant of the header material in the human body over time. The ferrite core is part of the charging coil assembly 95, shown in FIG. 5B, which is positioned inside the ceramic case 94. The ferrite core concentrates the magnetic field flux through the ceramic case as opposed to the metallic case portion 97. This configuration maximizes coupling efficiency, which reduces the required magnetic field and in turn reduces device heating during charging. In particular, because the magnetic field flux is oriented in a direction perpendicular to the smallest metallic cross section area, heating during charging is minimized. It is appreciated that these IPG structures and neurostimulation leads are described for illustrative purposes and that the anchoring structures described herein may be used with various other neurostimulation leads and IPGs in accordance with the principles of the invention.

The proximal end of the lead include a plurality of conductors corresponding to the plurality of electrodes at the distal end that electrically couple with corresponding contacts within the connector stack 93 within the header portion 91, thereby electrically connecting the IPG contacts with the neurostimulation electrodes 30 of the lead 20 for delivery of neurostimulation therapy. Although movement in the lower back region where the IPG is located is limited, the lead may still be subjected to forces and slight movement for various reasons, for example due to changes in tissue volume, trauma to the tissue region in which the system is implanted, or routine muscle movements. When these forces and movements are repeated over time, the connection between the proximal portion of the lead and the IPG may become compromised due to the fatigue caused by repeated stress and strain at the point of the stiffness mismatch that exists at the junction of the flexible lead and the IPG header portion 91. In some embodiments, a strain relief element that extends along a proximal portion of the lead where the lead exits the header portion 91 is included to provide strain relief at the junction of the proximal portion of the lead and the IPG so as to maintain integrity of the electrical connection and lengthen the useful life of the lead.

In some embodiments, the system includes a strain relief element that extends along a proximal portion of the lead adjacent the head portion of the IPG. The strain relief element may be disposed about the proximal portion of the lead or integrated into the lead itself. The strain relief element may include a proximal base that attaches or interfaces with a head portion of the IPG. In some embodiments, the strain relief element is a helical element that extends about the proximal portion of the lead. The strain relief element may be formed of a metal (e.g. stainless steel), polymer or any other suitable material. The proximal portion of the lead may include a recessed portion in which the strain relief element reside so that the outer surface of the strain relief element is substantially flush or about flush with the outer surface of the lead. Alternatively, the strain relief element may be applied to a non-recessed or standard sized portion anywhere along the lead body as needed. Typically, the strain relief element is a length within a range of about 1 inch to 6 inches so as to reduce flexing or bending of the proximal portion of the lead near the IPG, which can compromise the electrical connection over time. In one aspect, the strain relief element is formed so as to have an increased stiffness along a longitudinal axis so as to inhibit lateral bending of the proximal portion of the lead. Any of the aspects described herein in regard to the structure and design of the helical anchor body may be applicable to the strain relief element.

Figure 6A:
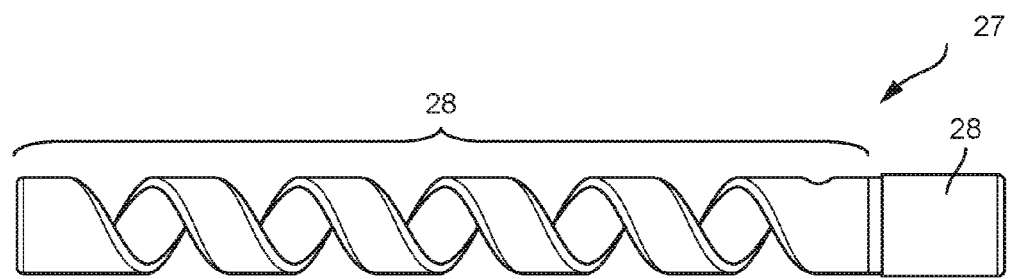
FIGS. 6A-6C show a strain relief structure for use with a neurostimulation lead and implantable pulse generator, in accordance with aspects of the invention.
Figure 6B:
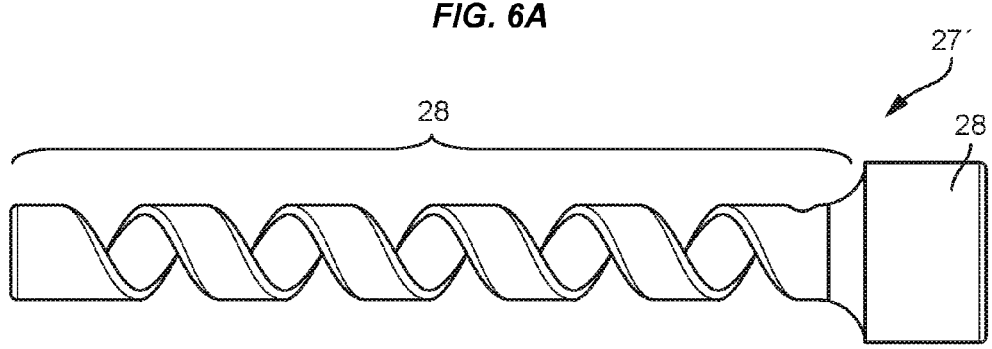
Figure 6C:
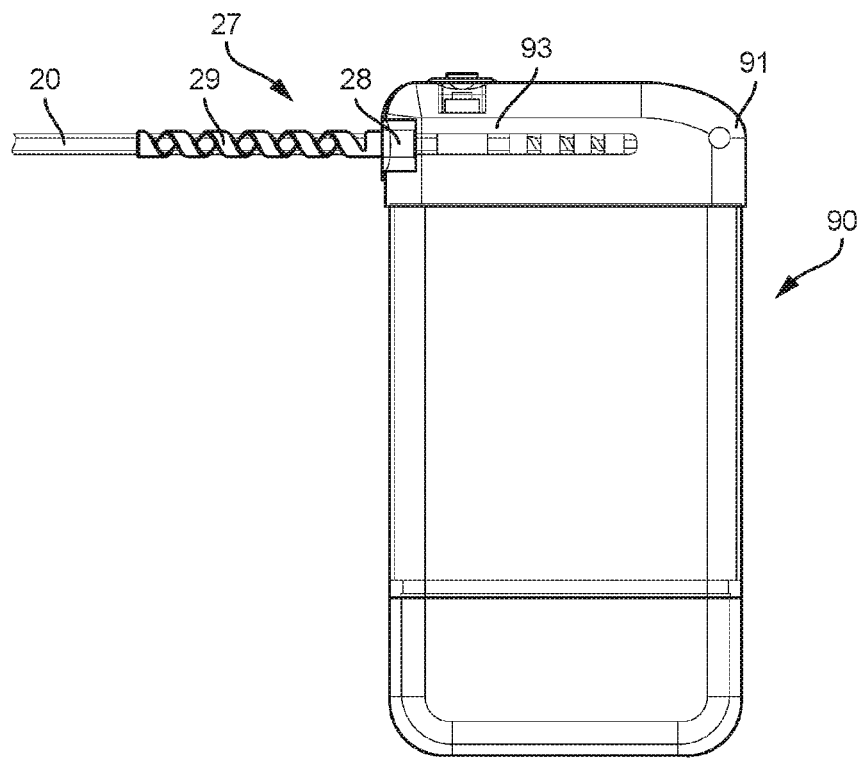

In some embodiments, the strain relief element 27 comprises a helical structure that extends along a proximal portion of the lead 20 adjacent where the lead 20 is inserted into the head portion 91 of the IPG 90, such as shown in FIG. 6C. The strain relief element 27 may include a proximal base 28 configured to securely attach to the header portion 91 and a helical portion 29 that encircles a proximal portion of the lead. Typically, the helical portion 29 exhibits increased stiffness as compared to the lead such that the helical portion 29 withstands any stresses or forces applied to the lead in the proximal region. Furthermore the helical structure limits the minimum bending radius in the region, which prevents sharp bends that can potentially damage the lead at the strain relief location. The strain relief element may be formed of any suitable, biocompatible material, including polymers or various metals (e.g. stainless steel, Nitinol). The strain relief member can be attached to the lead at manufacturing or alternatively, loaded onto the lead at the time of implant and attachment to the IPG connector.

In one aspect, the strain relief element is sufficiently thin such that its low profile does not substantially increase the maximum cross-section or crossing profile of the lead through the sheath. In some embodiments, the proximal portion of the lead may have a reduced diameter and dimension so as to fittingly receive the strain relief member so that the strain relief member is substantially flush with the outer surface of the lead distal of the strain relief member.

FIGS. 6A-6B illustrate detail views of example strain relief members 27 and 27', respectively, each including a proximal base 28 for securing to the IPG header portion and a helical strain relief portion 29 for wrapping about the proximal portion of the lead 20. The proximal base portion 28 may be sized and dimensioned according to a particular IPG header portion. In one aspect, the helical portions 29 can be configured to provide variable stiffness along the length of the proximal portion of the lead. For example, the helical portions 29 can be of variable thickness along the length of the strain relief to provide gradual stiffness transition in the region and/or the helical portions can vary in pitch and/or width along the length of the strain relief to provide gradual stiffness and limit the bend radius in the region. In another aspect, the strain relief element 27 can include one or more tines (not shown), similar to the anchors described herein, so as to provide tissue fixation to the strain relief portion and further inhibit movement or migration of the proximal portion of the lead.

III. Lead Affixation by Helical Anchors

Figure 7:
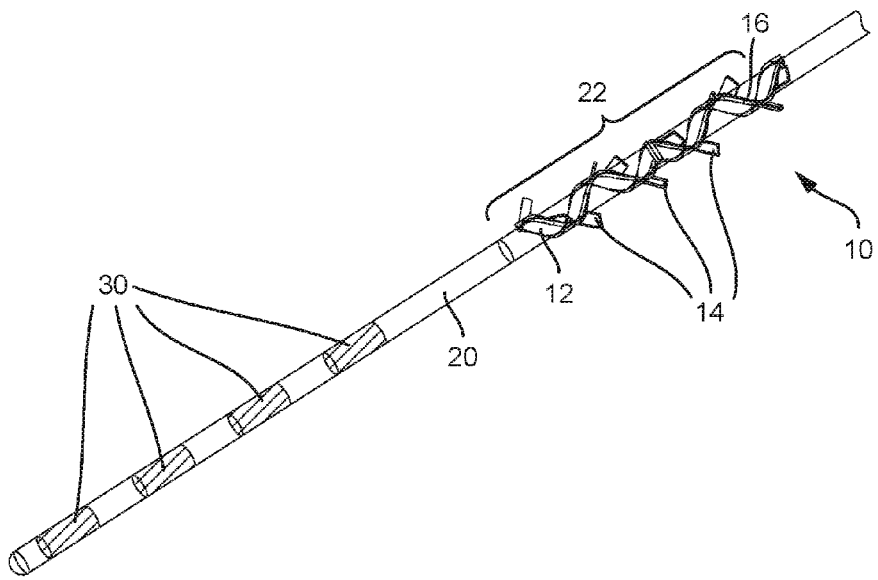
FIG. 7 illustrates a neurostimulation lead with an anchor structure thereon, in accordance with aspects of the invention.

FIG. 7 illustrates a detail view of a neurostimulation lead 20, similar to that in FIG. 4, with an anchoring body 10 mounted on an anchoring portion 22 of the lead, shown in the deployed configuration. As can be seen, the helical body 12 is helically swept about a central longitudinal axis for placement on the lead body and the plurality of tines 14 are distributed along the helical body 12 extending laterally outward from the central axis and angled in a proximal direction. As shown in the detail view of 10 FIG. 8, the plurality of tines 14 of the anchoring body are distributed so as to be radially offset from one another at regular intervals (e.g. 30°, 45°, 90°) within a range of intervals, such as between 10° and 90°, so that the plurality of tines extend outward in different directions circumferentially about the central axis. This distributes any anchoring forces about the lead body so as to improve anchoring of the lead.

In one aspect, the anchor 10 includes a radiopaque strip 16 embedded within the helical body 12 to allow localization of the anchor 10 through visualization techniques. The radiopaque strip may be fabricated from any radiopaque material, such as a platinum alloy (e.g. Pt/Ir), so as to visible using standard visualization techniques. Such a strip is advantageous as it facilitates positioning of the lead at the targeted location. In other embodiments, the helical body may be formed of a material that is radiopaque, for example a radiopaque material may be blended into a polymer material of which the anchor is formed.

FIGS. 9A-9B illustrate a neurostimulation lead having an attached anchor in a delivery configuration and a deployed configuration, respectively. In FIG. 9A, the plurality of tines 14 are folded against the body of the lead 20 without overlapping each other or an adjacent section of the helical body. Typically, the tines are constrained in the delivery configuration by an outer sheath (not shown) while the lead is advanced through a tunnel in a tissue to the targeted location. The helical body is swept at a pitch to allow sufficient space between adjacent turns of the helical body for a tab to fold inward against the lead boy, which allows for a reduced delivery profile. In one aspect, the cross section of the anchor is less than 2.0 mm, sufficiently small to be delivered through a 5 French sheath. In one aspect, the lead body includes a recessed portion 22 having a reduced outer diameter, in which the helical body 12 is attached. This feature facilitates coupling between the anchor 10 and the lead body 20 as the proximal and distal ends of the anchor abut against the proximal and distal ends of the recessed portion and allow for a reduced cross-section or crossing profile of the anchor portion of the lead. Once delivery of the electrodes to the target location is confirmed, the sheath may be withdrawn proximally, thereby allowing the plurality of tines to resiliently return to the deployed configuration toward which they are biased, as shown in FIG. 9B.

FIGS. 10A-10B illustrate detail views of the anchor 10 shown in FIG. 9B in the deployed configuration. In this embodiment, the tines 14 are all inclined proximally. It is understood, however, that in other embodiments, the anchor 10 may be configured so that the tines are angled distally or proximally, extend perpendicular to the longitudinal axis of the helical body, or extend in multiple differing directions as desired for a particular application.

In one aspect, the anchor is fabricated from a material sufficiently stiff to exert adequate anchoring forces to maintain the lead in place, yet sufficiently flexibly to fold inward against the lead and to avoid damaging tissue should the lead be removed from the tissue. In some embodiments, the anchor is fabricated from a molded polyurethane having a shore hardness within a range between 50A and 80D, preferably about 70D. The helical body may have a width between 1.0 mm to 3.0 mm, preferably about 2.0 mm and a total length between 10 mm and 30 mm, preferably about 20 mm. The anchor is configured such that the crossing profile is less than 2.0 mm, preferably 1.7 mm or less, so that a lead having the anchor attached thereto can be delivered through a standard sheath, such as a 5 French sheath. In certain embodiments, the tines have a length between 1 mm and 3 mm, preferably about 1.8 mm; a width between 0.5 and 2.0 mm, preferably about 0.8 mm; and a thickness between 0.2 mm and 0.5 mm, preferably about 0.3 mm. In certain embodiments, the anchor includes between 10 and 20 tines, preferably about 12 to 16 tines, spaced apart along the length of the helical body so as to extend in different directions circumferentially about the lead. In some embodiments, the tines are all of the same length and angle in the same direction, while in other embodiments, the tines may be of varying lengths, widths and may angle in both proximal and distal directions. While it is advantageous to dimension any of the anchor described herein according to the above described configuration in order to facilitate delivery of the anchor through a 5 French sheath, it is appreciated that the anchor may be configured according to various other dimensions (length, number of tines, etc.) as desired for a particular application or neurostimulation lead.

Figure 8:
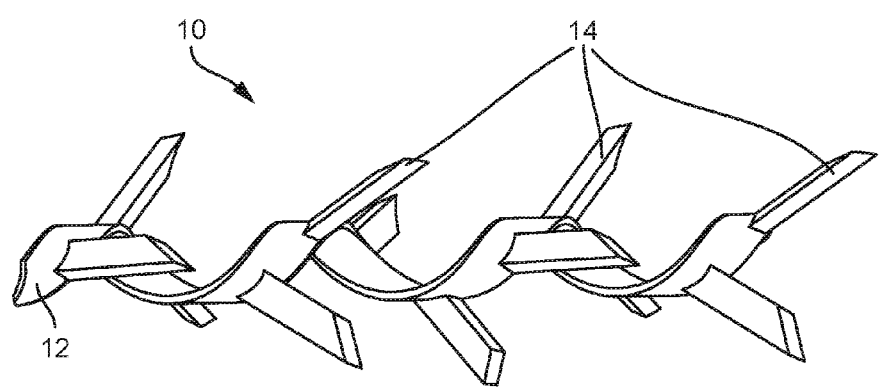
FIG. 8 illustrates an example anchor structure, in accordance with aspects of the invention.
Figure 11A:
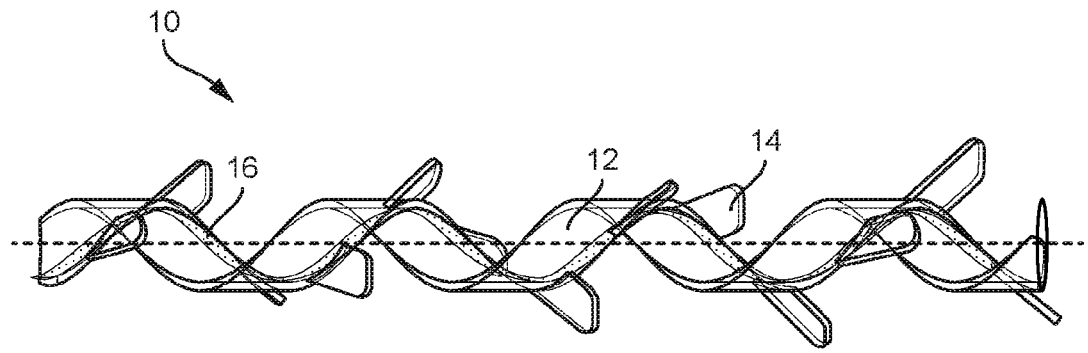
FIGS. 11A-11B illustrate an example anchor structure, in accordance with aspects of the invention.
Figure 11B:
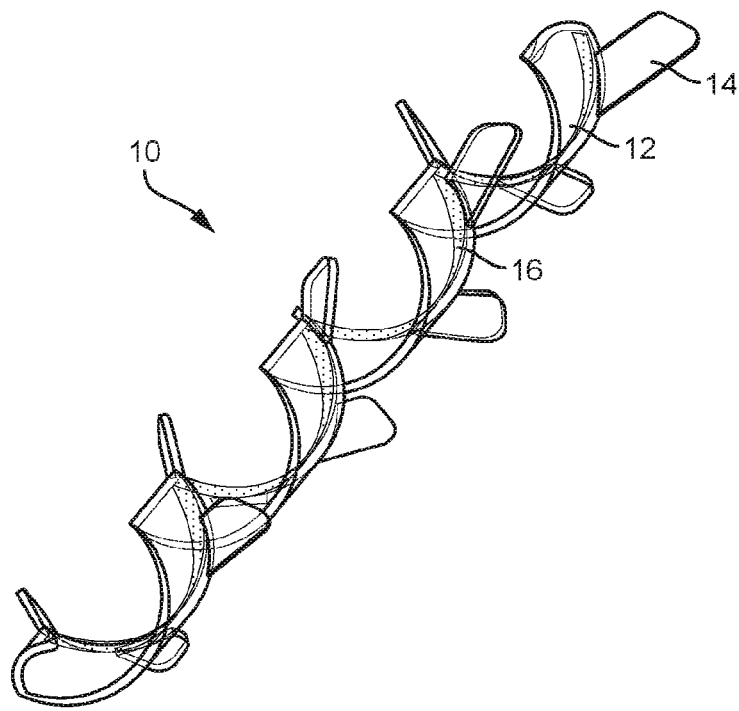

FIGS. 10A-10B and 11A-11B illustrate example anchors, similar to that shown in FIG. 8, except the tines 14 are formed in differing shapes. For example, in one aspect, the tines may be formed such that an end face is angled or pointed, such as shown in FIG. 8. In another aspect, the tines can be formed in a generally rectangular shape, such as shown in FIGS. 10A-10B. In another aspect, the tines can be formed such that the corners and/or edges are curved, rounded or chamfered, such as shown in FIGS. 11A-11B. This feature may help reduce the possibility of trauma to adjacent tissues by corners or edges of the tines as they engage tissue during anchoring of the lead.

Figure 12A:
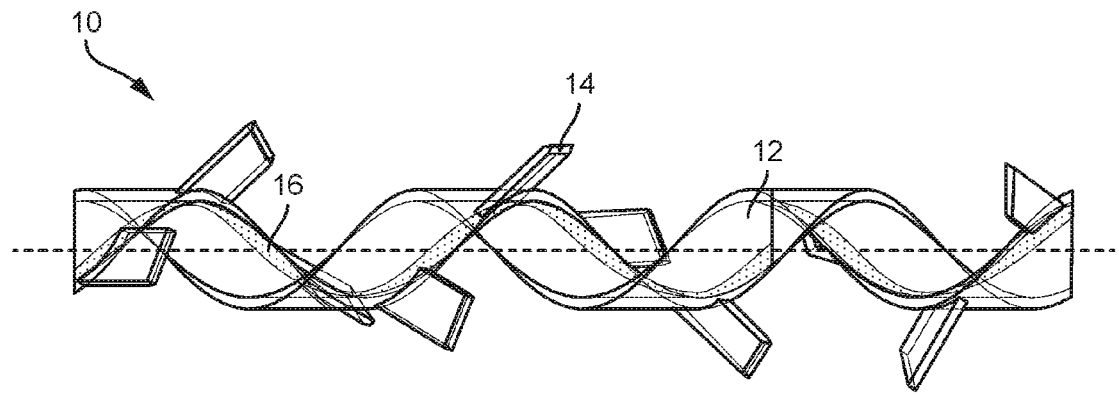
FIGS. 12A-12B illustrate an example anchor structure, in accordance with aspects of the invention.
Figure 12B:
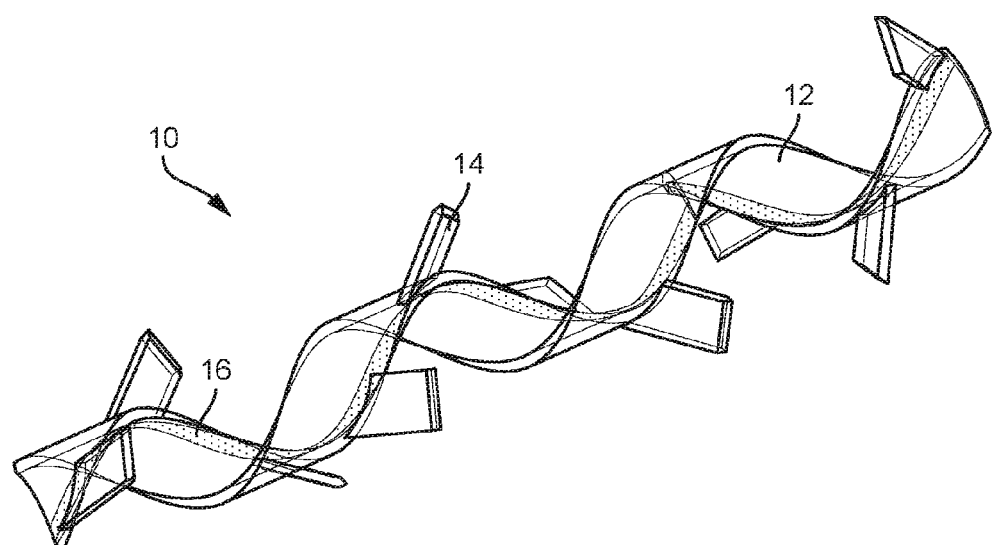

FIGS. 12A-12B illustrate an example anchor similar to that in FIG. 8 except the plurality of tines angle in both proximal and distal directions. As can be seen, the proximal most tines angle in a distal direction, while the remaining tines angle in a proximal direction. This aspect is useful in applications where the lead tends to experience forces in both proximal and distal directions. For example, while studies have shown that neurostimulation leads implanted through a sacral foramen experience primarily forces directed in a proximal direction, various other applications, such as a peripherally implanted lead in an arm or leg, may experience significant forces in both proximal and distal directions.

Figure 13A:
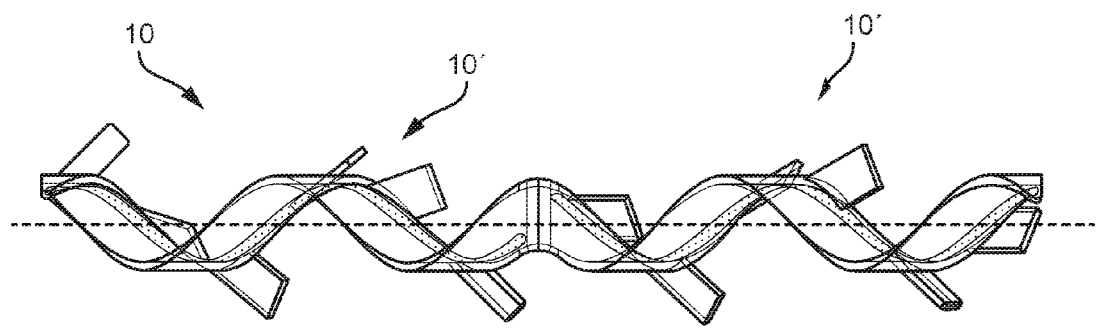
FIGS. 13A-13B illustrate an example anchor structure, in accordance with aspects of the invention.
Figure 13B:
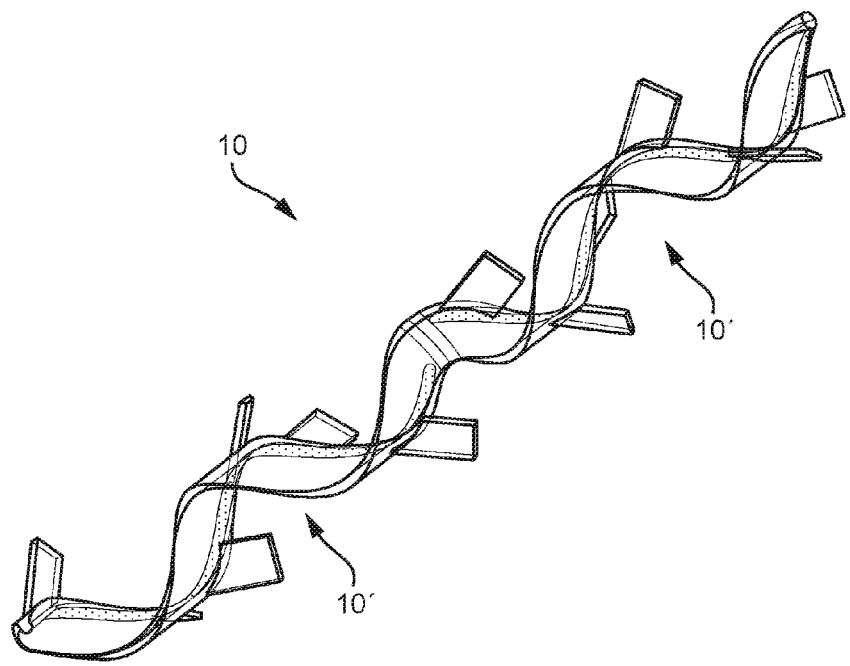

FIGS. 13A-13B illustrate an anchor 10 composed of multiple anchor sections 10'. As shown, the anchor consists of two sections joined together. The anchor sections 10' may be modular allowing one or more anchor sections to be used on a lead, as needed for a particular lead or application. The anchor sections may include a means to attach or couple the sections to one another or may be bonded together by various methods known to one of skill in the art, such as by use of an adhesive, a mechanical or chemical coupling, or an oxidation bonding method. This feature may allow a user to customize an anchoring portion with as desired, according to differing lengths, as well as differing dimensions and/or directions of the tines.

FIG. 14A-14B illustrates an anchor 10 having a cork-screw type shape. The anchor includes a continuous helical flap having multiple sections defined by cuts into the helical flap into multiple sections that can fold toward the lead body without overlapping one another. In one aspect, the anchor 10 is formed from monolithically from a single integral component. For example, the anchor 10 may be formed from a cork-screw type structure in which the helical flap is separated into tines by wedge-shaped notches 15 cut into the helical flap to define multiple tines 14 that can fold down against the lead for delivery of the anchor through a constraining insertion sheath.

In another aspect, any of the anchors described herein may include one or more various other features, including: biodegradable tines, drug eluting tines, and flexible dish-like tines that open or collapse after a certain bend angle is reached to allow for easy insertion or retraction. In another aspect, the anchor may include a strip or embedded material that shield or disrupts Mill induced heating.

In one aspect, the anchor 10 includes one or more drug eluting components, that release one or more therapeutic compounds over a period of time after implantation. Such a drug eluting component may include a portion of the anchor, a strip intertwined along a length of the anchor, the material from which the anchor is formed, or a coating deposited on the anchor or portion thereof. For example, the drug or therapeutic compound can be sprayed onto the anchor, the anchor can be dipped in the drug or compound, or the drug or compound can be mixed into a polymer of which the anchor is formed. In some embodiments, the anchor may be formed of a bioabsorable or nonabsorable polymer material or a combination of a nonabsorable base coated with a layer of drug eluting polymer. In one aspect, the drug or therapeutic compound may be applied in order to promote release of the drug in particular direction, for example the drug or compound may be applied to promote isotropic or anisotropic release of the drug along the axis of the tines. The eluting drug may be selected to promote and shorten healing time in order to minimize risk of lead migration. Alternatively or in addition to, the anchor may be configured to elute various other drugs to provide various other therapeutic benefits. For example, the anchor 10 may be formed to elute a compound to promote fixation within the tissues, such as a biological adhesive or compound to promote tissue formation after implantation in order to further minimize risk of lead migration.

While in many of the embodiments shown, the tines are configured to protrude and fold along an axis parallel to the longitudinal axis along which the helical portion extends, in some embodiments, the anchor can be designed so that the tines fold inward along a helical or inclined axis. Such a configuration can allow the tines to be retracted by twisting the lead in one direction to facilitate removal of the lead and/or allow the tines to be further deployed by twisting the lead in an opposite direction. In other embodiments, such as those in which the tines fold along an axis parallel to the longitudinal axis, the tines may be sufficiently flexible and/or frangible to allow removal of the lead by merely retracting the lead with sufficient force.

Figure 15A:
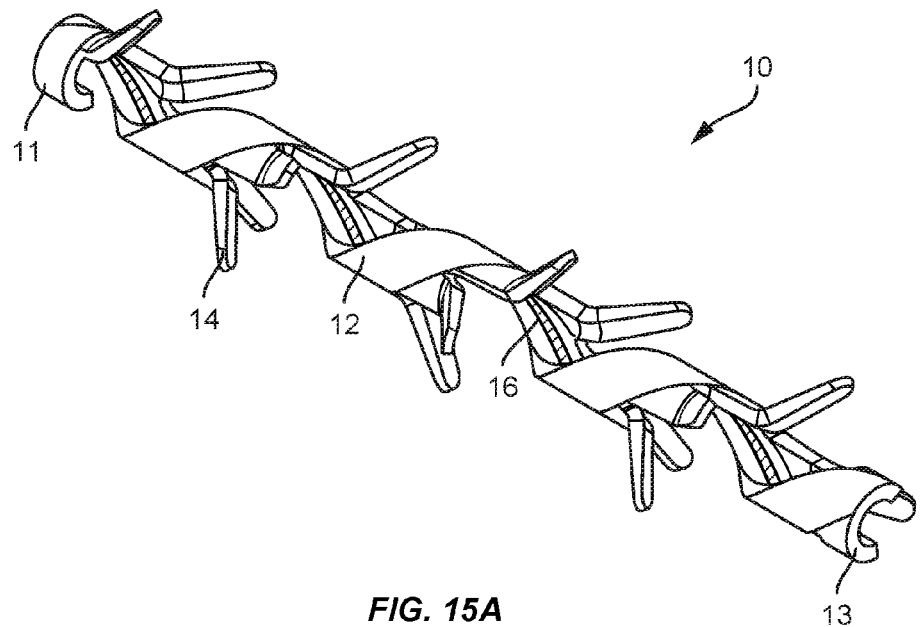
FIGS. 15A-15C illustrate an example anchor structure before and after deployment and FIG. 15C illustrates an end view of the deployed anchor structure, in accordance with aspects of the invention.
Figure 15B:
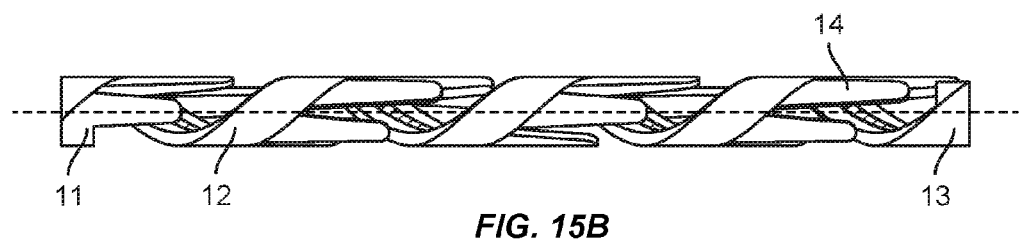
Figure 15C:
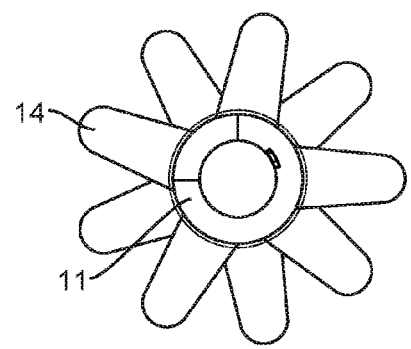

In one aspect, the anchor may be formed by cutting a pattern into an integral piece of material, for example a shape-memory metal, such as Nitinol. For example, the anchor can be formed by laser cutting a helical pattern into a piece of tubing or a cylindrical piece of the material, the pattern corresponding to the anchor in the constrained configuration, such as shown in the example of FIG. 15B. The tines can then be supported on a mold or propped up by various other means so that the material can be heat set while the anchor is in the expanded configuration, such as shown in FIG. 15A. Typically, the pattern is defined so that the tines are distributed evenly along the length of the helical body with the tines extending out in a multi-radial direction along the sweep of the spiral to provide evenly distributed tissue fixation in all directions, as shown in FIG. 15C.

In one aspect, the helical base can be heat set to a smaller inside diameter than the lead body so as to provide an interference fit, which can then be twisted to open and then loaded onto the lead body. Upon release, the helical base automatically tightens onto the lead body providing a secure attachment to the lead. The spiral design is configured so that when the tines are folded down the tines do not overlap each other or the helical body of the anchor.

In another aspect, as shown in FIG. 15A, the anchor design can include one or more retention features 11, 13 at the proximal and distal ends, respectively, that enable precise loading of the anchor onto the device. In this embodiment, the proximal and distal retention features 11,13 are designed to abut against a corresponding proximal and distal end of a reduced diameter anchoring portion 22 of the lead in which the anchor 10 is received so as to affix the anchor 10 to the body of the lead 20 and prevent axial movement of the anchor 10 along the lead before, during and/or after delivery of the lead and deployment of the anchor 10. In another aspect, the proximal and distal retention features 11, 13 may be designed in various shapes (e.g. zig-zag, curved, angled) along the proximal and distal facing edges so as to interlock with corresponding shapes along the lead at the proximal and distal ends of the anchoring portion 22. This configuration is useful in preventing free rotational movement of the anchor 10 relative the lead body 20 or to assist in translating rotational movement to the anchor upon rotation of the lead.

In one aspect, the anchor 10 may be formed of any type of implantable biocompatible polymers. Radiopaque fillers such as barium sulfate, bismuth, and tungsten can be added to the polymer to make the tines radiopaque under x-ray. Alternatively, or in addition to, a ribbon of radiopaque metal such as gold or platinum can be imbedded into the body of the helix to add radiopacity to the tines. In another approach, the anchor may include one or more discrete radiopaque markers that can be used with visualization techniques for localization of the anchor or that can be used to determine when the tines are deployed. For example, by placing one of a pair of markers at the end of a tine and the other on the helical body directly adjacent the end of the tine, when the anchor is in the constrained configuration, separation of the pair of markers can indicate when the tines are deployed, as well as the extent of their deployment within the tissue.

Figure 16A:
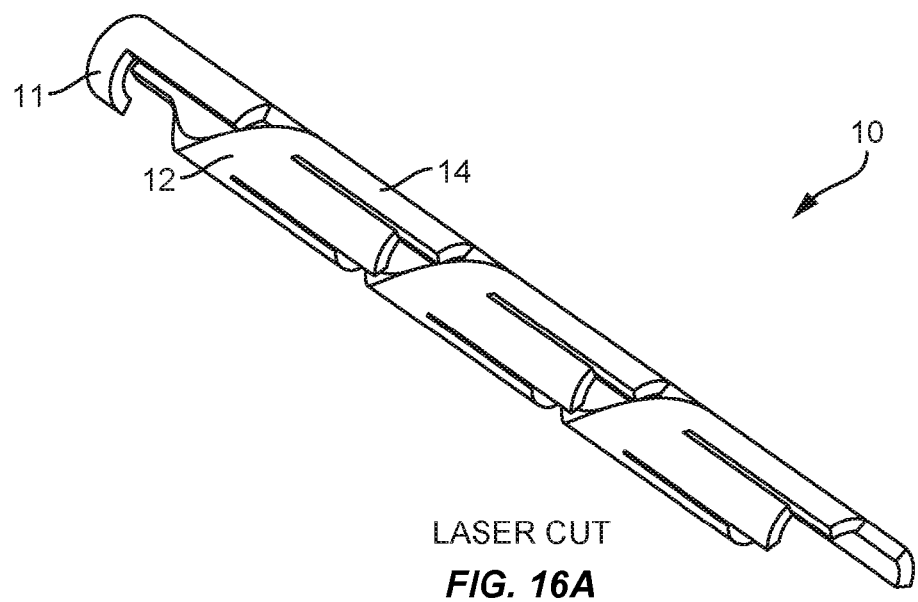
FIGS. 16A-16B illustrate an example anchor structure formed by laser cutting, the structure shown before and after deployment, in accordance with aspects of the invention.
Figure 16B:
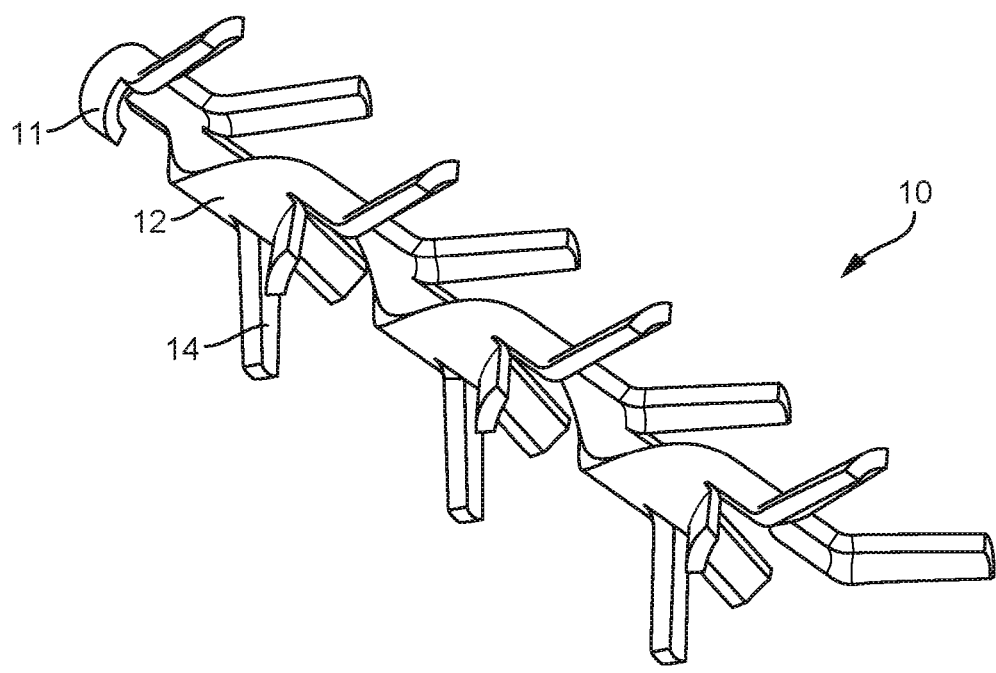

FIG. 16A illustrate another approach by which the anchor 10 can be formed. As shown in FIG. 16A, the anchor may be cut from a length of extruded polymer tubing, for example by laser cutting. The tines can be subsequently shaped to have an outwardly protruding bias through a heat set or reflow process. For example, the anchor 10 can be mounted on an internal mold (not shown) that props up the tines in an outwardly protruding configuration corresponding to the deployed anchor configuration and the polymer is heated and allowed to set. After setting, the tines 14 of the anchor 10 are biased towards the deployed configuration, such as shown in FIG. 16B. In one aspect, this heating and reflow process can also be used to incorporate one or more radiopaque markers, such as a Pt/Ir wire or ribbon wrapped at the same pitch as the helix. In another aspect, the polymer tubing extrusion can incorporate a ribbon or coil (e.g. nitinol or gold) ribbon to provide self expanding or self closure shape memory element to the anchor tines. Laser cutting can be programming to cut around the embedded ribbon wire to include the wire into the body of the helix.

Figure 17A:
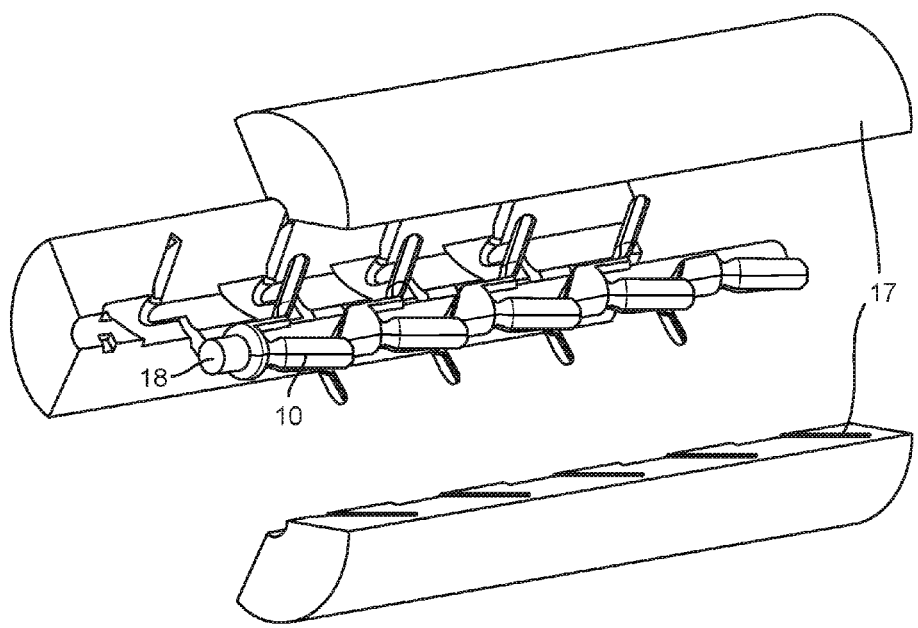
FIGS. 17A-17B illustrate an alternative illustrate an example anchor structure formed by an injection molding process, in accordance with aspects of the invention.
Figure 17B:
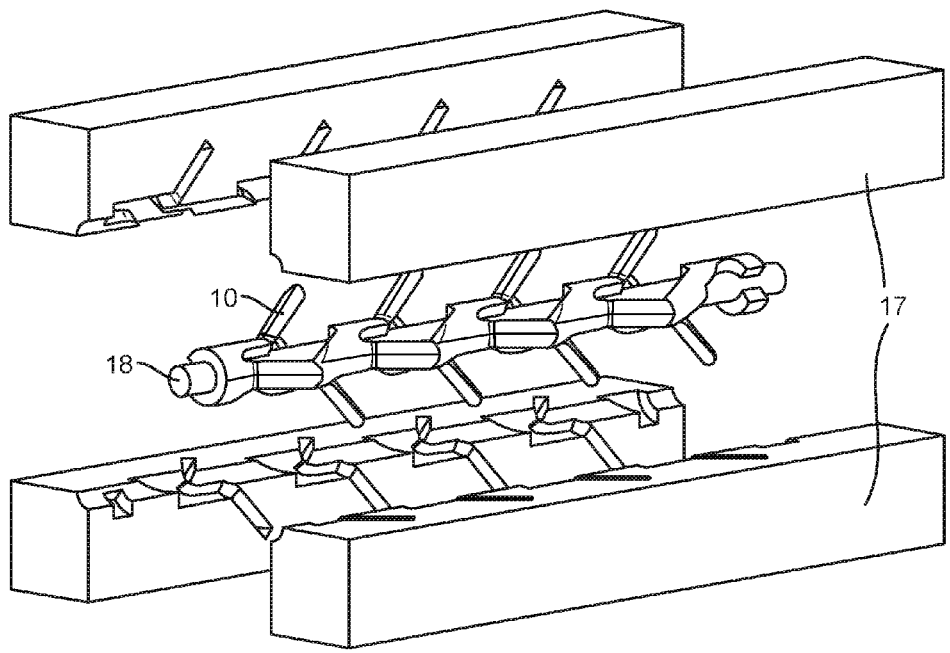

FIG. 17A-17B illustrate yet another approach by which the anchor 10 may be formed. Helical anchors, such as any of those described herein, can be formed by injection molding using a multi-piece mold design. For example, two, three or four piece mold designs can be used to mold the anchors as a single integral component. In one aspect, the mold can be configured so as to release the anchor at an angle that is specific to the design of the anchors. A shown in FIG. 17A, a three-piece mold 17 is used to form anchor 10 by an injection molding process. A core pin 18 is used along with the mold to form the open lumen of the anchor. FIG. 17B shows a four piece mold design 17' also configured for use with the core pin 18 to allow formation of an anchor 10 through an injection molding process. One advantage to using an injection molding process to form the anchor, is that molded anchors can have variable thickness along the length of the component. For example, such an anchor can be formed so that the base is thinner to improve crossing profile and the protruding tines are thicker to provide retention strength after implantation. In another aspect, a metallic element can be incorporated along the entire length, at the location of the tines, or in the distal and proximal ends for radiopacity.

Figure 18:
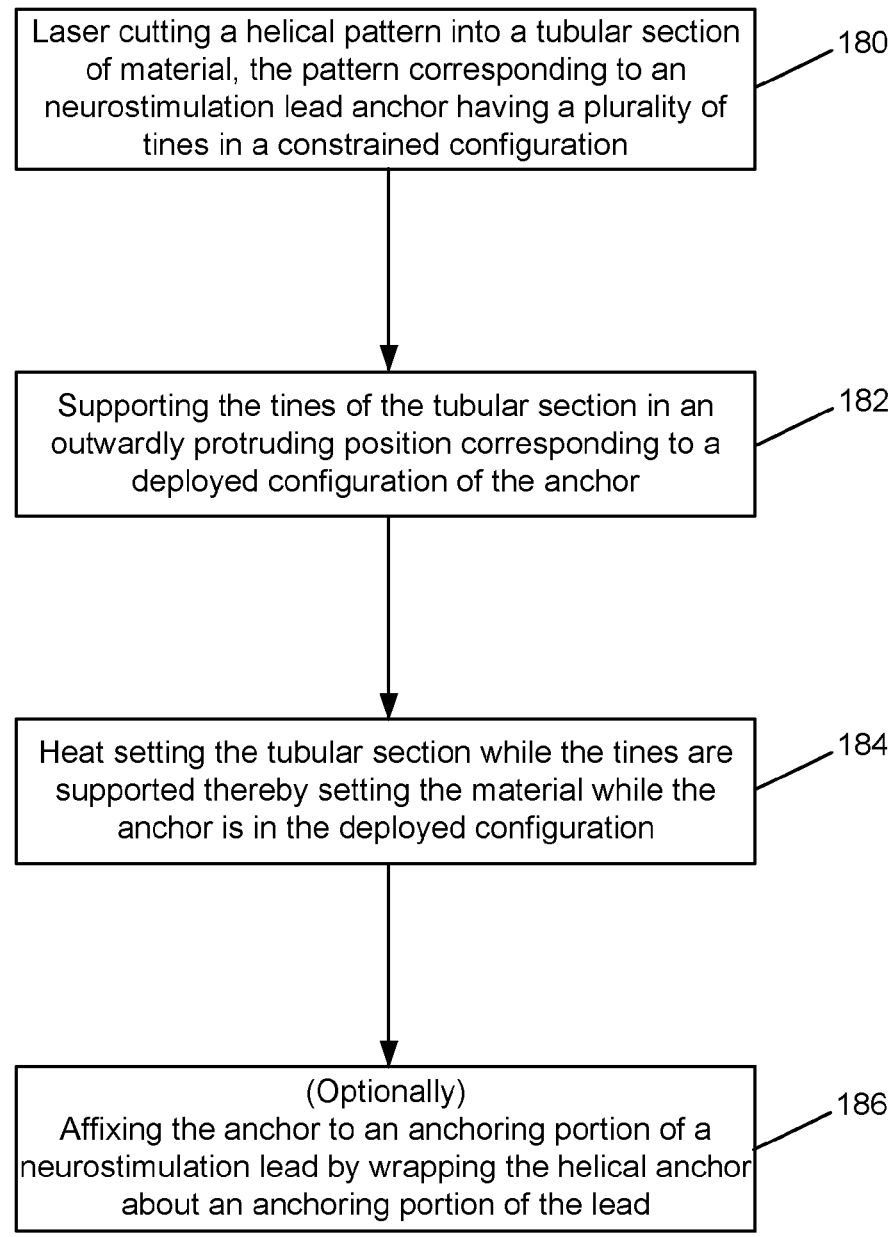
FIGS. 18-20 illustrate methods of forming an anchor and methods of anchoring a neurostimulation lead in accordance with aspects of the invention.
Figure 19:
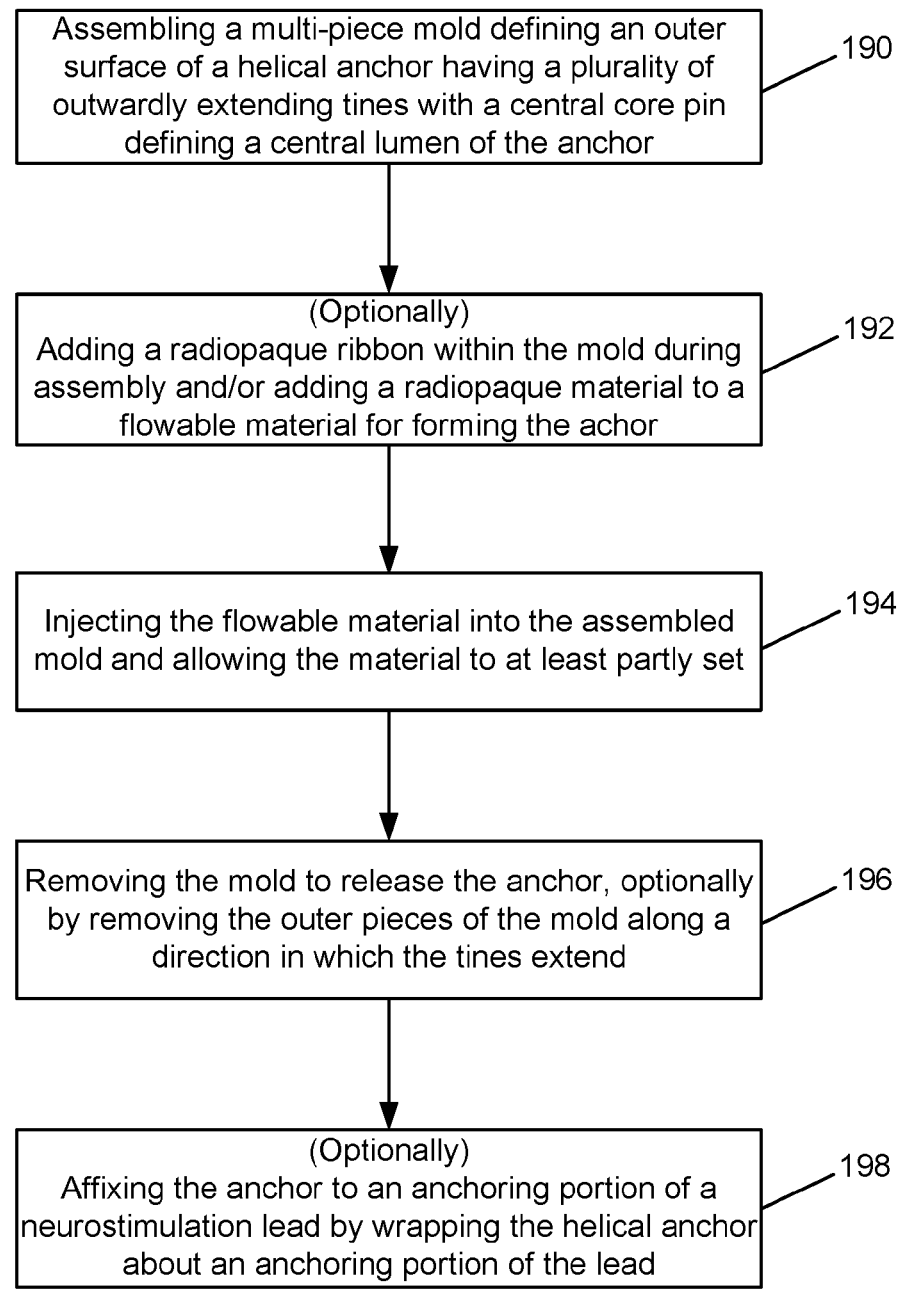

Methods of forming anchor in accordance with aspects of the invention described above are shown in the examples of FIG. 18-19. The example method of FIG. 18 includes method steps of: laser cutting a helical pattern into a tubular section of material, the pattern corresponding to an neurostimulation lead anchor having a plurality of tines in a constrained configuration 180; supporting the tines of the tubular section in an outwardly protruding position corresponding to a deployed configuration of the anchor 182; and heat setting the tubular section while the tines are supported thereby setting the material while the anchor is in the deployed configuration 184. In one aspect, the material is Nitinol, preferably in the superelastic phase and having an austenitic finish temperature from about 15 degrees C. to about 35 degrees C., so that the anchor will return to the deployed configuration upon heating in the body. In another aspect, the material may be formed of a polymer material that can be set in the deployed configuration by heating and reflow. The methods may be provided to a user to apply to the lead, or may be affixed to the lead before shipment to the user by wrapping the anchor about an anchoring portion 186. The example method of FIG. 19 includes steps of: assembling a multi-piece mold defining an outer surface of a helical anchor having a plurality of outwardly extending tines with a central core pin defining a central lumen of the anchor 190; injecting the flowable material into the assembled mold and allowing the material to at least partly set 194; and removing the mold to release the anchor 196. In some embodiments, the molds are configured such that the outer pieces of the mold are removed along a direction in which the tines extend, which reduces the stress and forces applied to the tines during removal. In some embodiments, a radiopaque ribbon within the mold during assembly and/or adding a radiopaque material to a flowable material for forming the anchor 192. Again, the anchor may be provided to the user for assembly with the lead or applied to the lead 198 and supplied to the user assembled with the lead. In another aspect, the anchor may be provided with the lead within a constraining sheath ready for insertion into the patient according to the implantation methods described herein.

Figure 20:
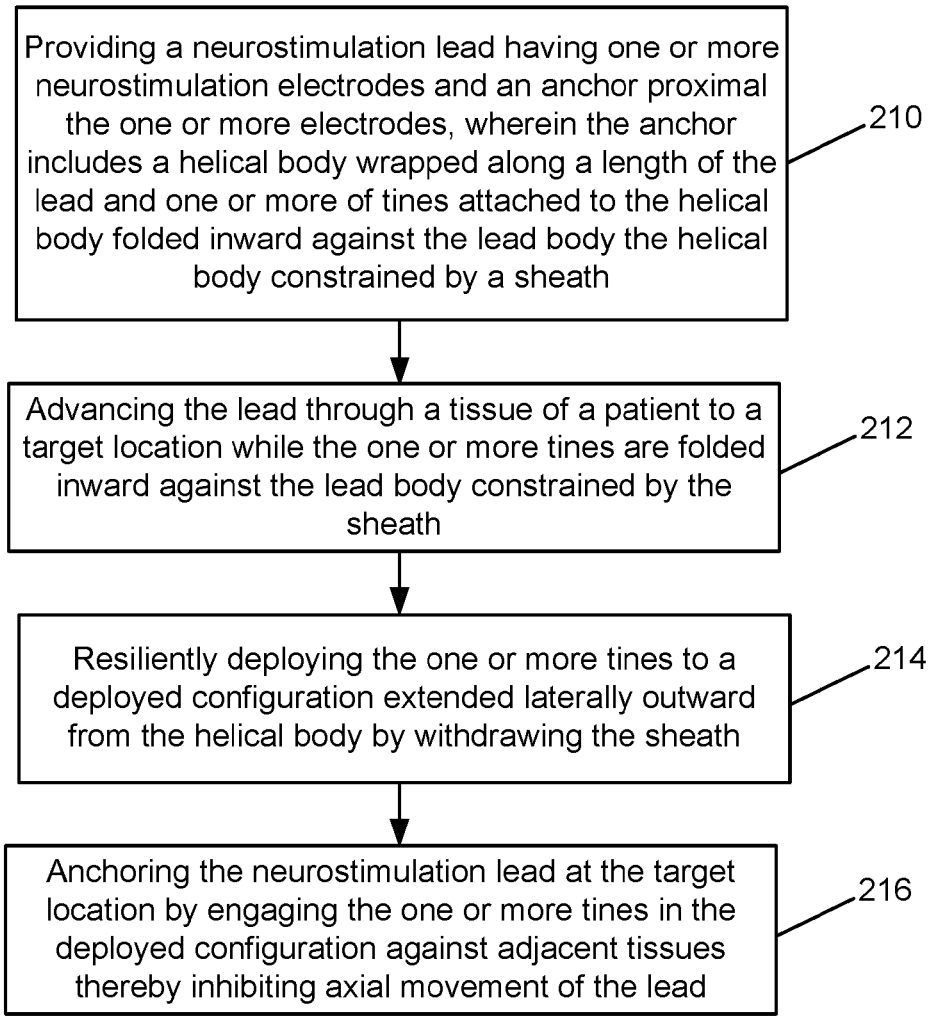

Methods of affixing an implanted neurostimulation lead using an anchor in accordance with aspects of the invention are show in the examples of FIGS. 20-21. The example method of FIG. 20 includes steps of: providing a neurostimulation lead having one or more neurostimulation electrodes and an anchor proximal the one or more electrodes, the anchor including a helical body wrapped along a length of the lead and one or more of tines attached to the helical body folded inward against the lead body the helical body constrained by a sheath 210; advancing the lead through a tissue of a patient to a target location while the one or more tines are folded inward against the lead body constrained by the sheath 212; resiliently deploying the one or more tines to a deployed configuration extended laterally outward from the helical body by withdrawing the sheath 214; and anchoring the neurostimulation lead at the target location by engaging the one or more tines in the deployed configuration against adjacent tissues thereby inhibiting axial movement of the lead 216. Lead removal may be effected by proximally withdrawing the lead until the anchoring force provided by the flexible tines is overcome. Thus, the tines are fabricated from a material having sufficient stiffness to provide a desired anchoring force but flexible enough to avoid tissue damage when withdrawn.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A neurostimulation lead comprising:
   an implantable lead having a plurality of conductors disposed within a lead body, the plurality of conductors extending from a proximal end of the lead to a plurality of neurostimulation electrodes disposed at or near a distal end of the lead, each conductor of the plurality corresponding to a respective neurostimulation electrode of the plurality of neurostimulation electrodes; and
   a single anchor coupled with the lead body and configured for anchoring the implanted lead within a body of a patient, wherein the lead includes only the single anchor, the anchor comprising:
      a helical body extending helically on the outside of the lead body along a longitudinal axis and disposed along a recessed portion of the lead body, and
      a plurality of tines extending from the helical body, wherein each of the plurality of tines is biased toward a deployed configuration, wherein in the deployed configuration, the plurality of tines extend laterally away from the longitudinal axis, and the plurality of tines are resiliently deflectable toward a delivery configuration in which the plurality of tines are folded inward toward the longitudinal axis to facilitate delivery of the neurostimulation lead during implantation, wherein the recessed portion, the helical body and the plurality of tines are dimensioned to facilitate fine-tuned placement of the lead in delivery and deployment.

2. The neurostimulation lead of claim 1, wherein the anchor is configured such that in the delivery configuration, each of the plurality of tines is folded against the lead body.

3. The neurostimulation lead of claim 1, wherein the anchor is dimensioned such that, in the delivery configuration, the anchor has a cross sectional profile compatible with a sheath having a 5 French diameter or higher.

4. The neurostimulation lead of claim 1, wherein the helical body and the plurality of tines are integrally formed.

5. The neurostimulation lead of claim 1, wherein the anchor is formed of a material with sufficient stiffness so that engagement of tissue with the plurality of tines inhibits axial movement of the lead when implanted in a tissue of the patient at the target location.

6. The neurostimulation lead of claim 5, wherein the anchor is molded from a polyurethane based material having a shore hardness in a range from 50A to 80D.

7. The neurostimulation lead of claim 1, wherein the anchor is dimensioned so that the helical body extends a length ranging from 10 mm to 30 mm along a distal portion of the lead body when coupled thereon.

8. The neurostimulation lead of claim 1, wherein the anchor is disposed entirely proximal of the plurality of neurostimulation electrodes.

9. The neurostimulation lead of claim 1, wherein the anchor is the one and only anchor on the neurostimulation lead.

10. The neurostimulation lead of claim 1, wherein, in the deployed configuration, each of the plurality of tines extends laterally outward from the longitudinal axis a distance within range from 1 mm to 4 mm.

11. The neurostimulation lead of claim 1, wherein each of the plurality of tines range from 1.5 mm to 3 mm in length and each of the plurality of tines range from 0.5 mm to 2.0 mm in width.

12. The neurostimulation lead of claim 11, wherein the plurality of tines include tines of varying length or width.

13. The neurostimulation lead of claim 1, wherein the anchor is dimensioned so that a proximal and distal end of the helical body abut against proximal and distal ends of the recessed portion.

14. The neurostimulation lead of claim 13, wherein each of the plurality of tines has an elongate shape and has rounded or chamfered corners and/or edges so as to inhibit tissue damage.

15. The neurostimulation lead of claim 1, wherein, in the deployed configuration, each of the plurality of tines extends laterally outward from the longitudinal axis at an angle ranging from 30 to 80 degrees from the longitudinal axis.

16. The neurostimulation lead of claim 1, wherein, in the deployed configuration, each of the plurality of tines are angled in a proximal direction.

17. The neurostimulation lead of claim 1, wherein, in the deployed configuration, the plurality of tines are angled in both a proximal direction and a distal direction.

18. The neurostimulation lead of claim 1, wherein, when in the delivery configuration, the anchor has a cross sectional profile of 2 mm or less.

19. A neurostimulation lead comprising:
an implantable lead having a lead body and one or more neurostimulation electrodes disposed at or near a distal end of the lead; and
a single anchor coupled to the lead body, wherein the anchor is formed as a single integral component and configured for anchoring the implanted lead within a body of a patient, the anchor comprising:
a spiral body wrapped on a portion of the lead body along a longitudinal axis thereof and disposed entirely within a recessed portion of the lead body, and
a plurality of tines extending from the spiral body, wherein each of the plurality of tines extends laterally outward and is resiliently deflectable to allow for a reduced profile delivery configuration when constrained by a sheath to facilitate delivery of the neurostimulation lead during implantation,
wherein the recessed portion, the spiral body and the plurality of tines are dimensioned to facilitate fine-tuned placement of the lead in delivery and deployment.

20. A neurostimulation lead comprising:
an implantable lead having a lead body and at least four neurostimulation electrodes disposed at or near a distal end of the lead; and
an anchor coupled with the lead body and configured for anchoring the lead within a body of a patient to maintain the at least four neurostimulation electrodes at or near a target tissue location, the anchor comprising:
a helical body attached to the lead body along a recessed portion thereof and extending helically along a longitudinal axis thereof, and
a plurality of tines extending from the helical body, wherein each of the plurality of tines extends laterally away from longitudinal axis of the helical body, when in a deployed configuration, so as to facilitate anchoring of the lead, and wherein each of the plurality of tines is deflectable inward towards the lead body in a constrained configuration to allow a reduced delivery profile to facilitate implantation of the lead
wherein the anchor is dimensioned so that an outer surface of the helical body is substantially flush with an outer surface of the lead body outside of the recessed portion so as to improve ease and accuracy in delivery and positioning during deployment to facilitate fine-tuned lead placement.

21. The neurostimulation lead of claim 20, wherein the anchor is configured such that in the delivery configuration, each of the plurality of tines is folded against the lead body so as to provide improved consistency in delivery profile along the anchor to facilitate fine-tuned lead placement.

22. The neurostimulation lead of claim 19, wherein the anchor is configured such that in the delivery configuration, each of the plurality of tines is folded against the lead body so as to provide improved consistency in delivery profile along the anchor to facilitate fine-tuned lead placement.

23. The neurostimulation lead of claim 1, wherein the plurality of tines are distributed along the helical body so as to facilitate fine-tuned placement of the lead upon deployment.

24. The neurostimulation lead of claim 19, wherein the plurality of tines are distributed along the spiral body so as to facilitate fine-tuned placement of the lead upon deployment.

25. The neurostimulation lead of claim 20, wherein the plurality of tines are distributed along the helical body so as to facilitate fine-tuned placement of the lead upon deployment.

\* \* \* \* \*